US010729469B2

(12) United States Patent
Jackson

(10) Patent No.: US 10,729,469 B2
(45) Date of Patent: Aug. 4, 2020

(54) FLEXIBLE SPINAL STABILIZATION ASSEMBLY WITH SPACER HAVING OFF-AXIS CORE MEMBER

(76) Inventor: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 12/584,980

(22) Filed: Sep. 15, 2009

(65) Prior Publication Data

US 2010/0010542 A1 Jan. 14, 2010

Related U.S. Application Data

(63) Continuation-in-part of application No. 12/221,442, filed on Aug. 1, 2008, which is a continuation-in-part of application No. 11/328,481, filed on Jan. 9, 2006, now Pat. No. 7,862,587, application No. 12/584,980, which is a continuation-in-part of application No. 12/069,577, filed on Feb. 11, 2008, now abandoned, and a continuation-in-part of application No. 11/894,001, filed on Aug. 17, 2007.

(60) Provisional application No. 61/192,312, filed on Sep. 17, 2008, provisional application No. 61/210,058, filed on Mar. 13, 2009, provisional application No. 60/900,816, filed on Feb. 12, 2007, provisional application No. 60/997,079, filed on Oct. 1, 2007, provisional application No. 60/851,353, filed on Oct. 12, 2006.

(51) Int. Cl.
*A61B 17/70* (2006.01)

(52) U.S. Cl.
CPC ........ *A61B 17/7008* (2013.01); *A61B 17/701* (2013.01); *A61B 17/702* (2013.01); *A61B 17/7032* (2013.01)

(58) Field of Classification Search
CPC . A61B 17/7008; A61B 17/701; A61B 17/702; A61B 17/7032; A61B 17/7046
USPC .................................................. 606/246–279
See application file for complete search history.

(56) References Cited

U.S. PATENT DOCUMENTS

| | | | |
|---|---|---|---|
| 854,956 A | 5/1907 | Martin |
| 2,243,717 A | 5/1941 | Moreira |
| 2,346,346 A | 4/1944 | Anderson |
| 2,362,999 A | 11/1944 | Elmer |
| 2,531,892 A | 11/1950 | Reese |
| 2,813,450 A | 11/1957 | Dzus |

(Continued)

FOREIGN PATENT DOCUMENTS

| | | |
|---|---|---|
| CA | 2577436 | 6/2006 |
| DE | 9202745.8 | 4/1992 |

(Continued)

OTHER PUBLICATIONS

Brochure of Sofamor Danek the Spine Specialist, TSRH, Pedicle Screw Spinal System, Publication Date: Jan. 23, 1995.

(Continued)

*Primary Examiner* — Nicholas J Plionis
(74) *Attorney, Agent, or Firm* — Polsinelli PC

(57) ABSTRACT

A flexible stabilization assembly includes a flexible inner core, an outer spacer with an off-axis lumen that receives the inner core, and at least one end cap located on either end of the spacer and rotationally fixed with respect to the spacer. Bone screws cooperating with the end cap and spacer include structure for close cooperation and engagement with the end cap. When implanted, the flexible inner core is posteriorly biased with respect to the spacer.

9 Claims, 15 Drawing Sheets

(56) References Cited

U.S. PATENT DOCUMENTS

| | | |
|---|---|---|
| 3,013,244 A | 12/1961 | Rudy |
| 3,236,275 A | 2/1966 | Smith |
| 3,604,487 A | 9/1971 | Gilbert |
| 3,640,416 A | 2/1972 | Temple |
| 4,033,139 A | 7/1977 | Frederick |
| 4,041,939 A | 8/1977 | Hall |
| 4,190,091 A | 2/1980 | Colognori |
| 4,373,754 A | 2/1983 | Bollfrass et al. |
| 4,448,191 A | 5/1984 | Rodnyansky et al. |
| 4,484,570 A | 11/1984 | Sutter et al. |
| 4,600,224 A | 7/1986 | Blose |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,790,297 A | 12/1988 | Luque |
| 4,836,196 A | 6/1989 | Park et al. |
| 4,877,020 A | 10/1989 | Vich |
| 4,887,596 A | 12/1989 | Sherman |
| 4,946,458 A | 8/1990 | Harms et al. |
| 4,950,269 A | 8/1990 | Gaines, Jr. |
| 5,005,562 A | 4/1991 | Cotrel |
| 5,019,080 A | 5/1991 | Hemer |
| 5,020,519 A | 6/1991 | Hayes et al. |
| 5,022,791 A | 6/1991 | Isler |
| 5,034,011 A | 7/1991 | Howland |
| 5,042,982 A | 8/1991 | Harms et al. |
| 5,067,955 A | 11/1991 | Cotrel |
| 5,084,048 A | 1/1992 | Jacob et al. |
| 5,092,635 A | 3/1992 | DeLange et al. |
| 5,092,866 A | 3/1992 | Breard et al. |
| 5,102,412 A | 4/1992 | Rogozinski |
| 5,129,388 A | 7/1992 | Vignaud et al. |
| 5,147,363 A | 9/1992 | Harle |
| 5,154,719 A | 10/1992 | Cotrel |
| 5,171,279 A * | 12/1992 | Mathews ............... A61B 17/70 128/898 |
| 5,176,483 A | 1/1993 | Baumann et al. |
| 5,176,678 A | 1/1993 | Tsou |
| 5,176,679 A | 1/1993 | Lin |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,862 A | 2/1994 | Barker et al. |
| 5,282,863 A | 2/1994 | Burton |
| D346,217 S | 4/1994 | Sparker et al. |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,346,493 A | 9/1994 | Stahurski et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,409,488 A | 4/1995 | Ulrich |
| 5,409,489 A | 4/1995 | Sioufi |
| 5,414,661 A | 5/1995 | Holmes |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,466,238 A | 11/1995 | Lin |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,437 A | 1/1996 | Michelson |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,499,892 A | 3/1996 | Reed |
| 5,505,731 A | 4/1996 | Tornier |
| 5,507,745 A | 4/1996 | Logroscino et al. |
| 5,496,321 A | 5/1996 | Puno |
| 5,540,688 A | 7/1996 | Navas |
| 5,545,165 A | 8/1996 | Biedermann et al. |
| 5,549,607 A | 8/1996 | Olson et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,569,253 A | 10/1996 | Farris et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Biedermann et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,830 A | 7/1998 | Farris |
| 5,782,833 A | 7/1998 | Haider |
| 5,792,044 A | 8/1998 | Foley et al. |
| 5,797,911 A | 8/1998 | Sherman et al. |
| 5,800,435 A | 9/1998 | Errico et al. |
| 5,800,547 A | 9/1998 | Schafer et al. |
| 5,810,816 A | 9/1998 | Roussouly et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morison et al. |
| 5,902,231 A | 5/1999 | Foley et al. |
| RE36,221 E | 6/1999 | Breard et al. |
| 5,910,141 A | 6/1999 | Morrison et al. |
| 5,938,663 A | 8/1999 | Petreto |

(56) References Cited

U.S. PATENT DOCUMENTS

| | | |
|---|---|---|
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,912 A | 8/2000 | Cazin et al. |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,139,549 A | 10/2000 | Keller |
| 6,143,032 A | 11/2000 | Schafer et al. |
| 6,146,383 A | 11/2000 | Studer et al. |
| 6,183,472 B1 | 2/2001 | Lutz |
| 6,186,718 B1 | 2/2001 | Fogard |
| 6,187,005 B1 | 2/2001 | Brace et al. |
| 6,193,720 B1 | 2/2001 | Yuan et al. |
| 6,214,012 B1 | 4/2001 | Karpman et al. |
| RE37,161 E | 5/2001 | Michelson et al. |
| 6,224,596 B1 | 5/2001 | Brace et al. |
| 6,224,598 B1 | 5/2001 | Jackson |
| 6,235,028 B1 | 5/2001 | Brumfield et al. |
| 6,235,034 B1 | 5/2001 | Bray |
| 6,241,730 B1 | 6/2001 | Alby |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,146 B1 | 7/2001 | Church |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,277,122 B1 | 8/2001 | McGahan et al. |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,290,700 B1 | 9/2001 | Schmotzer |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,302,888 B1 | 10/2001 | Mellinger et al. |
| 6,309,391 B1 | 10/2001 | Crandall et al. |
| 6,315,564 B1 | 11/2001 | Levisman |
| 6,315,779 B1 | 11/2001 | Morrison et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,402,752 B2 | 6/2002 | Schaffler-Wachter et al. |
| 6,402,757 B1 | 6/2002 | Moore et al. |
| 6,440,137 B1 | 8/2002 | Horvath et al. |
| 6,443,956 B1 | 9/2002 | Ray |
| 6,451,021 B1 | 9/2002 | Ralph et al. |
| 6,471,703 B1 | 10/2002 | Ashman |
| 6,471,705 B1 | 10/2002 | Biedermann et al. |
| 6,478,801 B1 | 11/2002 | Ralph et al. |
| 6,485,491 B1 | 11/2002 | Farris et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,511,484 B2 | 1/2003 | Torode et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,539,826 B2 | 4/2003 | Oesterle et al. |
| 6,540,749 B2 | 4/2003 | Schafer et al. |
| 6,547,790 B2 | 4/2003 | Harkey, III et al. |
| 6,551,320 B2 | 4/2003 | Lieberman |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,038 B1 | 5/2003 | Morrison |
| 6,562,040 B1 | 5/2003 | Wagner |
| 6,565,565 B1 | 5/2003 | Yuan et al. |
| 6,565,567 B1 | 5/2003 | Haider |
| 6,572,618 B1 | 6/2003 | Morrison |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner |
| 6,595,993 B2 | 7/2003 | Doono et al. |
| 6,599,294 B2 | 7/2003 | Fuss et al. |
| 6,610,063 B2 | 8/2003 | Kumar et al. |
| 6,613,050 B1 | 9/2003 | Wagner et al. |
| 6,616,667 B1 | 9/2003 | Steiger et al. |
| 6,616,669 B2 | 9/2003 | Ogilvie |
| 6,623,485 B2 | 9/2003 | Doubler et al. |
| 6,626,347 B2 | 9/2003 | Ng |
| 6,626,907 B2 | 9/2003 | Campbell et al. |
| 6,626,908 B2 | 9/2003 | Cooper et al. |
| 6,635,059 B2 | 10/2003 | Randall et al. |
| 6,635,060 B2 | 10/2003 | Hanson et al. |
| 6,648,885 B1 | 11/2003 | Friesem |
| 6,648,887 B2 | 11/2003 | Ashman |
| 6,648,888 B1 | 11/2003 | Shluzas |
| 6,652,526 B1 | 11/2003 | Arafiles |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,660,006 B2 | 12/2003 | Markworth et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,743,231 B1 | 6/2004 | Gray et al. |
| 6,746,449 B2 | 6/2004 | Jones et al. |
| 6,746,454 B2 | 6/2004 | Winterbottom et al. |
| 6,755,829 B1 | 6/2004 | Bono et al. |
| 6,755,835 B2 | 6/2004 | Schultheiss et al. |

(56) References Cited

U.S. PATENT DOCUMENTS

| | | |
|---|---|---|
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,778,861 B1 | 8/2004 | Liebrecht et al. |
| 6,780,186 B2 | 8/2004 | Errico et al. |
| 6,783,527 B2 | 8/2004 | Drewry et al. |
| 6,790,208 B2 | 9/2004 | Oribe et al. |
| 6,790,209 B2 | 9/2004 | Beale et al. |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,857,343 B1 | 2/2005 | Easterbrooks et al. |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,896,677 B1 | 5/2005 | Lin |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| 7,044,947 B2 | 2/2006 | Shluzus et al. |
| RE39,035 E | 3/2006 | Finn et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,052,497 B2 | 5/2006 | Sherman et al. |
| 7,056,321 B2 | 6/2006 | Pagliuca et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,118,576 B2 | 10/2006 | Gitis et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,264,621 B2 | 9/2007 | Coates et al. |
| 7,270,665 B2 | 9/2007 | Morrison et al. |
| 7,282,064 B2 | 10/2007 | Chin |
| 7,291,151 B2 | 11/2007 | Alvarez |
| 7,291,153 B2 | 11/2007 | Glascott |
| 7,294,127 B2 | 11/2007 | Hawkins et al. |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,329,258 B2 | 2/2008 | Studer |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,361,196 B2 | 4/2008 | Fallin et al. |
| 7,377,921 B2 | 5/2008 | Studer et al. |
| 7,476,238 B2 | 1/2009 | Panjabi |
| 7,556,639 B2 | 7/2009 | Rothman et al. |
| 7,559,942 B2 | 7/2009 | Paul et al. |
| 7,563,274 B2 | 7/2009 | Justis et al. |
| 7,563,283 B2 | 7/2009 | Kwak |
| 7,588,589 B2 | 9/2009 | Falahee |
| 7,601,166 B2 | 10/2009 | Biedermann et al. |
| 7,604,653 B2 | 10/2009 | Kitchen |
| 7,604,654 B2 | 10/2009 | Fallin et al. |
| 7,611,518 B2 | 11/2009 | Walder et al. |
| 7,615,068 B2 | 11/2009 | Timm et al. |
| 7,621,912 B2 | 11/2009 | Harms et al. |
| 7,621,940 B2 | 11/2009 | Harms et al. |
| 7,625,393 B2 | 12/2009 | Fallin et al. |
| 7,632,292 B2 | 12/2009 | Sengupta et al. |
| 7,641,673 B2 | 1/2010 | LeCouedic et al. |
| 7,651,515 B2 | 1/2010 | Mack et al. |
| 7,655,026 B2 | 2/2010 | Justis et al. |
| 7,658,739 B2 | 2/2010 | Shluzas |
| 7,658,752 B2 | 2/2010 | Labrom et al. |
| 7,682,375 B2 | 3/2010 | Ritland |
| 7,695,496 B2 | 4/2010 | Labrom et al. |
| 7,695,498 B2 | 4/2010 | Ritland |
| 7,695,514 B2 | 4/2010 | Kwak |
| 7,713,288 B2 | 5/2010 | Timm et al. |
| 7,763,048 B2 | 7/2010 | Fortin et al. |
| 7,763,052 B2 | 7/2010 | Jahng |
| 7,766,941 B2 | 8/2010 | Paul |
| 7,766,942 B2 | 8/2010 | Patterson et al. |
| 7,766,943 B1 | 8/2010 | Fallin et al. |
| 7,776,071 B2 | 8/2010 | Fortin et al. |
| 7,776,075 B2 | 8/2010 | Bruneau et al. |
| 7,785,349 B2 | 8/2010 | Walder et al. |
| 7,785,351 B2 | 8/2010 | Gordon et al. |
| 7,794,480 B2 | 9/2010 | Gordon et al. |
| 7,806,913 B2 | 10/2010 | Fanger et al. |
| 7,811,309 B2 | 10/2010 | Timm et al. |
| 7,815,663 B2 | 10/2010 | Trieu |
| 7,815,664 B2 | 10/2010 | Sherman et al. |
| 7,815,665 B2 | 10/2010 | Jahng et al. |
| 7,828,825 B2 | 11/2010 | Bruneau et al. |
| 7,842,072 B2 | 11/2010 | Dawson |
| 7,901,437 B2 | 3/2011 | Jackson |
| 7,988,710 B2 | 8/2011 | Jahng et al. |
| 8,029,544 B2 | 10/2011 | Hested et al. |
| 8,114,133 B2 | 2/2012 | Logan |
| 8,128,667 B2 | 3/2012 | Jackson |
| 8,157,843 B2 | 4/2012 | Biederman et al. |
| 8,292,926 B2 | 10/2012 | Jackson |
| 8,366,745 B2 | 2/2013 | Jackson |
| 8,465,526 B2 | 6/2013 | Friedrich et al. |
| 9,101,404 B2 | 8/2015 | Jackson |

(56) References Cited

U.S. PATENT DOCUMENTS

| | | |
|---|---|---|
| 9,439,683 B2 | 9/2016 | Jackson |
| 9,451,989 B2 | 9/2016 | Jackson |
| 9,861,394 B2 | 1/2018 | Jackson |
| 9,956,002 B2 | 5/2018 | Jackson |
| 2001/0001119 A1 | 5/2001 | Lombardo |
| 2001/0010000 A1 | 7/2001 | Gertzbein |
| 2001/0023350 A1 | 9/2001 | Choi |
| 2001/0029375 A1 | 10/2001 | Betz |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0035360 A1 | 3/2002 | Walder et al. |
| 2002/0035366 A1* | 3/2002 | Walder et al. ............ 606/61 |
| 2002/0045898 A1 | 4/2002 | Freid et al. |
| 2002/0055740 A1 | 5/2002 | Lieberman |
| 2002/0058942 A1 | 5/2002 | Biedermann et al. |
| 2002/0068975 A1 | 6/2002 | Teitelbaum et al. |
| 2002/0072751 A1 | 6/2002 | Jackson |
| 2002/0077701 A1 | 6/2002 | Kuslich |
| 2002/0082602 A1 | 6/2002 | Biedermann et al. |
| 2002/0095153 A1 | 7/2002 | Jones et al. |
| 2002/0107570 A1 | 8/2002 | Sybert et al. |
| 2002/0111626 A1 | 8/2002 | Ralph et al. |
| 2002/0116001 A1 | 8/2002 | Schafer |
| 2002/0116065 A1 | 8/2002 | Jackson |
| 2002/0133159 A1 | 9/2002 | Jackson |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2002/0198526 A1 | 12/2002 | Shaolian et al. |
| 2003/0023240 A1 | 1/2003 | Amrein et al. |
| 2003/0023243 A1 | 1/2003 | Biedermann et al. |
| 2003/0073996 A1 | 4/2003 | Doubler et al. |
| 2003/0083657 A1 | 5/2003 | Drewry et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0171749 A1 | 9/2003 | Le Douedic et al. |
| 2003/0176862 A1 | 9/2003 | Taylor et al. |
| 2003/0191470 A1 | 10/2003 | Ritland |
| 2003/0199873 A1 | 10/2003 | Richelsoph |
| 2003/0208203 A1 | 11/2003 | Lim et al. |
| 2003/0208204 A1 | 11/2003 | Bailey et al. |
| 2003/0212398 A1 | 11/2003 | Jackson |
| 2003/0216735 A1 | 11/2003 | Altarac et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2004/0002708 A1 | 1/2004 | Ritland |
| 2004/0006342 A1 | 1/2004 | Altarac et al. |
| 2004/0049189 A1 | 3/2004 | Le Couedic et al. |
| 2004/0049190 A1* | 3/2004 | Biedermann et al. ....... 606/61 |
| 2004/0073215 A1 | 4/2004 | Carli |
| 2004/0078082 A1 | 4/2004 | Lange |
| 2004/0220671 A1 | 4/2004 | Ralph et al. |
| 2004/0087949 A1 | 5/2004 | Bono et al. |
| 2004/0087952 A1 | 5/2004 | Borgstrom et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0133207 A1 | 7/2004 | Abdou |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0158247 A1 | 8/2004 | Sitiso et al. |
| 2004/0162560 A1 | 8/2004 | Raynor et al. |
| 2004/0167523 A1 | 8/2004 | Jackson |
| 2004/0172022 A1 | 9/2004 | Landry et al. |
| 2004/0172025 A1 | 9/2004 | Drewry et al. |
| 2004/0172032 A1 | 9/2004 | Jackson |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0215191 A1 | 10/2004 | Kitchen |
| 2004/0220567 A1 | 11/2004 | Eisermann et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249380 A1 | 12/2004 | Glascott |
| 2004/0260283 A1 | 12/2004 | Wu et al. |
| 2004/0267264 A1 | 12/2004 | Konieczynski et al. |
| 2005/0010220 A1 | 1/2005 | Casutt et al. |
| 2005/0027296 A1 | 2/2005 | Thramann et al. |
| 2005/0033298 A1 | 2/2005 | Hawkes et al. |
| 2005/0038432 A1 | 2/2005 | Shaolian et al. |
| 2005/0049708 A1 | 3/2005 | Atkinson et al. |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Johng |
| 2005/0065517 A1 | 3/2005 | Chin |
| 2005/0070899 A1 | 3/2005 | Doubler et al. |
| 2005/0080415 A1 | 4/2005 | Keyer et al. |
| 2005/0085812 A1 | 4/2005 | Sherman |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0096654 A1 | 5/2005 | Lin |
| 2005/0107788 A1 | 5/2005 | Beaurain et al. |
| 2005/0113927 A1 | 5/2005 | Malek |
| 2005/0124991 A1 | 6/2005 | Jahng |
| 2005/0131404 A1 | 6/2005 | Mazda et al. |
| 2005/0131407 A1 | 6/2005 | Sicvol et al. |
| 2005/0131413 A1 | 6/2005 | O'Driscoll et al. |
| 2005/0137597 A1 | 6/2005 | Butler et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165396 A1 | 7/2005 | Fortin et al. |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177157 A1 | 8/2005 | Jahng |
| 2005/0182401 A1 | 8/2005 | Timm et al. |
| 2005/0187548 A1 | 8/2005 | Butler et al. |
| 2005/0187555 A1 | 8/2005 | Beidermann et al. |
| 2005/0192571 A1 | 9/2005 | Abdelgany |
| 2005/0192580 A1 | 9/2005 | Dalton |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0216001 A1 | 9/2005 | David |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |

(56) References Cited

U.S. PATENT DOCUMENTS

| | | |
|---|---|---|
| 2005/0251140 A1 | 11/2005 | Shaolian et al. |
| 2005/0251141 A1 | 11/2005 | Frigg et al. |
| 2005/0260058 A1 | 11/2005 | Casagne, III |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267474 A1 | 12/2005 | Dalton |
| 2005/0267477 A1 | 12/2005 | Jackson |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277920 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277932 A1 | 12/2005 | Farris |
| 2005/0277934 A1 | 12/2005 | Vardiman |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brookmeyer et al. |
| 2006/0009767 A1 | 1/2006 | Kiester |
| 2006/0009768 A1 | 1/2006 | Ritland |
| 2006/0009769 A1 | 1/2006 | Lieberman |
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036256 A1 | 2/2006 | Carl et al. |
| 2006/0036259 A1 | 2/2006 | Carl et al. |
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak |
| 2006/0079898 A1 | 4/2006 | Ainsworth |
| 2006/0079899 A1 | 4/2006 | Ritland |
| 2006/0084977 A1 | 4/2006 | Liebermann |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0089643 A1 | 4/2006 | Mujwid |
| 2006/0089644 A1 | 4/2006 | Felix |
| 2006/0095037 A1 | 5/2006 | Jones et al. |
| 2006/0106380 A1 | 5/2006 | Colleran et al. |
| 2006/0106381 A1 | 5/2006 | Ferree |
| 2006/0106383 A1 | 5/2006 | Biedermann et al. |
| 2006/0111714 A1 | 5/2006 | Foley |
| 2006/0111715 A1 | 5/2006 | Jackson |
| 2006/0116677 A1 | 6/2006 | Burd et al. |
| 2006/0122597 A1 | 6/2006 | Jojnes et al. |
| 2006/0122599 A1 | 6/2006 | Drewry |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0142761 A1 | 6/2006 | Landry et al. |
| 2006/0149228 A1 | 7/2006 | Schlapfer |
| 2006/0149229 A1 | 7/2006 | Kwak |
| 2006/0149232 A1 | 7/2006 | Sasing |
| 2006/0149238 A1 | 7/2006 | Sherman et al. |
| 2006/0149241 A1 | 7/2006 | Richelsoph et al. |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189983 A1 | 8/2006 | Faliln |
| 2006/0189984 A1 | 8/2006 | Fallin |
| 2006/0189985 A1 | 8/2006 | Lewis |
| 2006/0195090 A1 | 8/2006 | Suddaby |
| 2006/0195093 A1 | 8/2006 | Jahng |
| 2006/0195198 A1 | 8/2006 | Schumacher |
| 2006/0200123 A1 | 9/2006 | Mueller |
| 2006/0200130 A1 | 9/2006 | Hawkins |
| 2006/0200131 A1 | 9/2006 | Chao et al. |
| 2006/0200132 A1 | 9/2006 | Chao et al. |
| 2006/0200135 A1 | 9/2006 | Sherman et al. |
| 2006/0200138 A1 | 9/2006 | Michelson |
| 2006/0200139 A1 | 9/2006 | Michelson |
| 2006/0200149 A1 | 9/2006 | Hoy et al. |
| 2006/0210494 A1 | 9/2006 | Rabiei et al. |
| 2006/0212033 A1 | 9/2006 | Rothman |
| 2006/0212034 A1 | 9/2006 | Triplett et al. |
| 2006/0217713 A1 | 9/2006 | Serhan et al. |
| 2006/0217714 A1 | 9/2006 | Serhan et al. |
| 2006/0217715 A1 | 9/2006 | Albert et al. |
| 2006/0217716 A1 | 9/2006 | Baker et al. |
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |

(56) References Cited

U.S. PATENT DOCUMENTS

| | | |
|---|---|---|
| 2006/0241602 A1 | 10/2006 | Jackson |
| 2006/0241603 A1 | 10/2006 | Jackson |
| 2006/0241769 A1 | 10/2006 | Gordon |
| 2006/0241771 A1 | 10/2006 | Gordon |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow |
| 2006/0247633 A1 | 11/2006 | Winslow |
| 2006/0247635 A1 | 11/2006 | Gordon |
| 2006/0247636 A1 | 11/2006 | Yuan et al. |
| 2006/0247637 A1 | 11/2006 | Colleran |
| 2006/0247779 A1 | 11/2006 | Gordon |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264937 A1 | 11/2006 | White |
| 2006/0264940 A1 | 11/2006 | Hartmannt |
| 2006/0264942 A1 | 11/2006 | Lim et al. |
| 2006/0264962 A1 | 11/2006 | Chin et al. |
| 2006/0269940 A1 | 11/2006 | Harman |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293665 A1 | 12/2006 | Shluzas |
| 2006/0293666 A1 | 12/2006 | Matthis et al. |
| 2007/0005062 A1 | 1/2007 | Lange |
| 2007/0005063 A1 | 1/2007 | Bruneau et al. |
| 2007/0005137 A1 | 1/2007 | Kwak |
| 2007/0016188 A1 | 1/2007 | Boehm, Jr. et al. |
| 2007/0016190 A1 | 1/2007 | Martinez |
| 2007/0016193 A1 | 1/2007 | Ritland |
| 2007/0016194 A1 | 1/2007 | Shaolian et al. |
| 2007/0016198 A1 | 1/2007 | Boehm, Jr. et al. |
| 2007/0016199 A1 | 1/2007 | Boehm, Jr. et al. |
| 2007/0021750 A1 | 1/2007 | Shluzas et al. |
| 2007/0043355 A1 | 2/2007 | Bette et al. |
| 2007/0043356 A1 | 2/2007 | Timm |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran |
| 2007/0055235 A1 | 3/2007 | Janowski et al. |
| 2007/0055236 A1 | 3/2007 | Hudgins |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0055247 A1 | 3/2007 | Jahng |
| 2007/0073289 A1 | 3/2007 | Kwak |
| 2007/0073290 A1 | 3/2007 | Boehm, Jr. |
| 2007/0073291 A1 | 3/2007 | Cordaro et al. |
| 2007/0073293 A1 | 3/2007 | Martz |
| 2007/0073405 A1 | 3/2007 | Chin et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0093813 A1 | 4/2007 | Callahan, II et al. |
| 2007/0093814 A1 | 4/2007 | Callahan, II et al. |
| 2007/0093815 A1 | 4/2007 | Callahan, II et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093827 A1 | 4/2007 | Warnick |
| 2007/0093828 A1 | 4/2007 | Abdou |
| 2007/0093831 A1 | 4/2007 | Abdelgany et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123867 A1 | 5/2007 | Kirschman |
| 2007/0123870 A1 | 5/2007 | Jeon et al. |
| 2007/0123871 A1 | 5/2007 | Jahng |
| 2007/0129729 A1 | 6/2007 | Petit et al. |
| 2007/0135815 A1 | 6/2007 | Gerbec et al. |
| 2007/0161986 A1 | 7/2007 | Levy |
| 2007/0161991 A1 | 7/2007 | Altarac et al. |
| 2007/0161994 A1 | 7/2007 | Lowery et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191839 A1 | 8/2007 | Justis et al. |
| 2007/0191841 A1* | 8/2007 | Justis .............. A61B 17/701 606/250 |
| 2007/0191846 A1 | 8/2007 | Bruneau et al. |
| 2007/0198014 A1 | 8/2007 | Graf et al. |
| 2007/0123720 A1 | 9/2007 | Gordon et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225710 A1 | 9/2007 | Jahng et al. |
| 2007/0225711 A1 | 9/2007 | Ensign |
| 2007/0233064 A1 | 10/2007 | Holt |
| 2007/0233073 A1 | 10/2007 | Wisnewski et al. |
| 2007/0233075 A1* | 10/2007 | Dawson ............ A61B 17/7008 606/86 A |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233087 A1 | 10/2007 | Schlapfer |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0250061 A1 | 10/2007 | Chin et al. |
| 2007/0124249 A1 | 11/2007 | Lim et al. |
| 2007/0260243 A1 | 11/2007 | Biedermann |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270814 A1 | 11/2007 | Lim et al. |
| 2007/0270815 A1 | 11/2007 | Johnson et al. |
| 2007/0270821 A1 | 11/2007 | Trieu et al. |
| 2007/0270830 A1 | 11/2007 | Morrison |

(56) References Cited

U.S. PATENT DOCUMENTS

| | | |
|---|---|---|
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270837 A1 | 11/2007 | Eckhardt et al. |
| 2007/0270838 A1 | 11/2007 | Bruneau et al. |
| 2007/0270840 A1 | 11/2007 | Chin et al. |
| 2007/0270843 A1 | 11/2007 | Matthis et al. |
| 2007/0276380 A1* | 11/2007 | Jahng ............... A61B 17/1757 606/86 A |
| 2007/0288004 A1 | 12/2007 | Alvarez |
| 2007/0288008 A1 | 12/2007 | Park |
| 2007/0288009 A1 | 12/2007 | Logan |
| 2007/0288011 A1 | 12/2007 | Logan |
| 2007/0288012 A1 | 12/2007 | Colleran et al. |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Norin et al. |
| 2008/0021465 A1 | 1/2008 | Shadduck et al. |
| 2008/0021466 A1 | 1/2008 | Shadduck et al. |
| 2008/0021469 A1 | 1/2008 | Holt |
| 2008/0021473 A1 | 1/2008 | Butler et al. |
| 2008/0027432 A1 | 1/2008 | Strauss et al. |
| 2008/0033435 A1 | 2/2008 | Studer et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0051787 A1* | 2/2008 | Remington et al. ............ 606/61 |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0071277 A1 | 3/2008 | Warnick |
| 2008/0077139 A1 | 3/2008 | Landry et al. |
| 2008/0086125 A1* | 4/2008 | Molz et al. .................. 606/61 |
| 2008/0086130 A1 | 4/2008 | Lake |
| 2008/0086131 A1 | 4/2008 | Daly et al. |
| 2008/0086132 A1 | 4/2008 | Biedermann et al. |
| 2008/0091214 A1 | 4/2008 | Richelsoph |
| 2008/0097431 A1 | 4/2008 | Vessa |
| 2008/0097434 A1 | 4/2008 | Moumene et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0119858 A1 | 5/2008 | Potash |
| 2008/0125777 A1 | 5/2008 | Veldman et al. |
| 2008/0125787 A1 | 5/2008 | Doubler et al. |
| 2008/0132952 A1 | 6/2008 | Malandain et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0147122 A1 | 6/2008 | Jackson |
| 2008/0154307 A1 | 6/2008 | Colleran et al. |
| 2008/0154308 A1 | 6/2008 | Sherman et al. |
| 2008/0234744 A1 | 6/2008 | Zylber et al. |
| 2008/0161854 A1 | 7/2008 | Bae et al. |
| 2008/0161857 A1 | 7/2008 | Hestad et al. |
| 2008/0161859 A1 | 7/2008 | Nilsson |
| 2008/0161863 A1 | 7/2008 | Arnold et al. |
| 2008/0167687 A1 | 7/2008 | Colleran et al. |
| 2008/0177316 A1 | 7/2008 | Bergeronk et al. |
| 2008/0177317 A1 | 7/2008 | Jackson |
| 2008/0177319 A1 | 7/2008 | Schwab |
| 2008/0177321 A1 | 7/2008 | Drewry et al. |
| 2008/0177322 A1 | 7/2008 | Davis et al. |
| 2008/0177327 A1 | 7/2008 | Malandain et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183219 A1 | 7/2008 | Jackson |
| 2008/0183223 A1 | 7/2008 | Jeon et al. |
| 2008/0195100 A1 | 8/2008 | Capote et al. |
| 2008/0195153 A1 | 8/2008 | Thompson |
| 2008/0215095 A1 | 9/2008 | Biedermann et al. |
| 2008/0221620 A1 | 9/2008 | Krause |
| 2008/0221692 A1 | 9/2008 | Zucherman et al. |
| 2008/0228227 A1 | 9/2008 | Brown et al. |
| 2008/0228229 A1 | 9/2008 | Walder et al. |
| 2008/0234691 A1 | 9/2008 | Schwab |
| 2008/0234734 A1 | 9/2008 | Wabler et al. |
| 2008/0234736 A1 | 9/2008 | Trieu et al. |
| 2008/0234737 A1 | 9/2008 | Bosehert |
| 2008/0234739 A1 | 9/2008 | Hudgins et al. |
| 2008/0234746 A1 | 9/2008 | Jahng et al. |
| 2008/0243188 A1 | 10/2008 | Walder |
| 2008/0255617 A1 | 10/2008 | Cho et al. |
| 2008/0262546 A1 | 10/2008 | Calvosa et al. |
| 2008/0262548 A1 | 10/2008 | Lange et al. |
| 2008/0262551 A1 | 10/2008 | Rice et al. |
| 2008/0262552 A1 | 10/2008 | Kim |
| 2008/0262553 A1 | 10/2008 | Hawkins et al. |
| 2008/0262554 A1 | 10/2008 | Hayes et al. |
| 2008/0269804 A1 | 10/2008 | Holt |
| 2008/0275504 A1 | 11/2008 | Bonin et al. |
| 2008/0287994 A1 | 11/2008 | Perez-Cruet et al. |
| 2008/0294198 A1 | 11/2008 | Jackson |
| 2008/0300630 A1 | 12/2008 | Bohnema et al. |
| 2008/0300633 A1 | 12/2008 | Jackson |
| 2008/0306528 A1 | 12/2008 | Winslow et al. |
| 2008/0306533 A1 | 12/2008 | Winslow et al. |
| 2008/0306536 A1 | 12/2008 | Frig et al. |
| 2008/0306539 A1 | 12/2008 | Cain et al. |
| 2008/0306540 A1 | 12/2008 | Mitchell et al. |
| 2008/0306543 A1 | 12/2008 | Cain et al. |
| 2008/0306545 A1 | 12/2008 | Winslow |
| 2008/0312694 A1 | 12/2008 | Peterman et al. |
| 2008/0319482 A1 | 12/2008 | Jackson |
| 2008/0319486 A1 | 12/2008 | Hestad et al. |
| 2009/0005817 A1 | 1/2009 | Friedrich et al. |
| 2009/0012562 A1 | 1/2009 | Hestad et al. |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030464 A1 | 1/2009 | Hestad et al. |
| 2009/0030465 A1 | 1/2009 | Altarac et al. |
| 2009/0036924 A1 | 2/2009 | Egli et al. |
| 2009/0048631 A1 | 2/2009 | Bhatnagar et al. |
| 2009/0054932 A1 | 2/2009 | Butler et al. |
| 2009/0069849 A1 | 3/2009 | Oh et al. |
| 2009/0082815 A1 | 3/2009 | Zylber et al. |
| 2009/0088799 A1 | 4/2009 | Yeh |
| 2009/0088803 A1 | 4/2009 | Justis et al. |
| 2009/0093820 A1 | 4/2009 | Trieu et al. |
| 2009/0093843 A1 | 4/2009 | Lemoine et al. |
| 2009/0093845 A1 | 4/2009 | Hestad et al. |
| 2009/0093846 A1 | 4/2009 | Hestad |
| 2009/0099606 A1 | 4/2009 | Hestad et al. |
| 2009/0099607 A1 | 4/2009 | Fallin et al. |
| 2009/0099608 A1 | 4/2009 | Szczesny |
| 2009/0105757 A1 | 4/2009 | Gimbel et al. |
| 2009/0105758 A1 | 4/2009 | Gimbel et al. |
| 2009/0105760 A1 | 4/2009 | Frey |
| 2009/0112265 A1 | 4/2009 | Hudgins et al. |
| 2009/0112266 A1 | 4/2009 | Weng et al. |
| 2009/0112267 A1 | 4/2009 | Atkinson et al. |
| 2009/0118767 A1 | 5/2009 | Hestad et al. |

(56) References Cited

U.S. PATENT DOCUMENTS

| | | |
|---|---|---|
| 2009/0125063 A1 | 5/2009 | Panjabi |
| 2009/0131981 A1 | 5/2009 | White |
| 2009/0138052 A1 | 5/2009 | Biedermann et al. |
| 2009/0149885 A1 | 6/2009 | Durwood et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0171395 A1 | 7/2009 | Jeon et al. |
| 2009/0177231 A1 | 7/2009 | Kiester |
| 2009/0177232 A1 | 7/2009 | Kiester |
| 2009/0192548 A1 | 7/2009 | Jeon et al. |
| 2009/0198280 A1 | 8/2009 | Spratt et al. |
| 2009/0198281 A1 | 8/2009 | Rice et al. |
| 2009/0204152 A1 | 8/2009 | Blain |
| 2009/0228045 A1 | 9/2009 | Hayes et al. |
| 2009/0240285 A1 | 9/2009 | Friedrich et al. |
| 2009/0240286 A1 | 9/2009 | Friedrich et al. |
| 2009/0240287 A1 | 9/2009 | Cunliffe et al. |
| 2009/0248075 A1 | 10/2009 | Ogilvie et al. |
| 2009/0248077 A1 | 10/2009 | Johns |
| 2009/0248081 A1 | 10/2009 | LeHuec et al. |
| 2009/0248083 A1 | 10/2009 | Patterson et al. |
| 2009/0248088 A1 | 10/2009 | Biedermann |
| 2009/0254123 A1 | 10/2009 | Pafford et al. |
| 2009/0259257 A1 | 10/2009 | Prevost |
| 2009/0259258 A1 | 10/2009 | Perez-Cruet et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275986 A1 | 11/2009 | Prevost et al. |
| 2009/0281572 A1 | 11/2009 | White |
| 2009/0281573 A1 | 11/2009 | Biedermann et al. |
| 2009/0287250 A1 | 11/2009 | Molz, IV et al. |
| 2009/0287251 A1 | 11/2009 | Bae et al. |
| 2009/0287252 A1 | 11/2009 | Marik et al. |
| 2009/0299411 A1 | 12/2009 | Laskowitz et al. |
| 2009/0318968 A1 | 12/2009 | Duggal et al. |
| 2009/0326582 A1 | 12/2009 | Songer et al. |
| 2009/0326583 A1 | 12/2009 | Moumene et al. |
| 2010/0010542 A1 | 1/2010 | Jackson |
| 2010/0010543 A1 | 1/2010 | Jackson |
| 2010/0010544 A1 | 1/2010 | Fallin et al. |
| 2010/0030271 A1 | 2/2010 | Winslow et al. |
| 2010/0036420 A1 | 2/2010 | Kalfas et al. |
| 2010/0036422 A1 | 2/2010 | Flynn et al. |
| 2010/0036423 A1 | 2/2010 | Hayes et al. |
| 2010/0036424 A1 | 2/2010 | Fielding et al. |
| 2010/0036425 A1 | 2/2010 | Barrus et al. |
| 2010/0042155 A1 | 2/2010 | Biedermann et al. |
| 2010/0042156 A1 | 2/2010 | Harms et al. |
| 2010/0049254 A1 | 2/2010 | Biedermann et al. |
| 2010/0057125 A1 | 3/2010 | Viker |
| 2010/0057126 A1 | 3/2010 | Hestad |
| 2010/0063544 A1 | 3/2010 | Butler |
| 2010/0063545 A1 | 3/2010 | Richelsoph |
| 2010/0063547 A1 | 3/2010 | Morin et al. |
| 2010/0063551 A1 | 3/2010 | Richelsoph |
| 2010/0069964 A1 | 3/2010 | Lechmann |
| 2010/0087858 A1 | 4/2010 | Abdou |
| 2010/0087862 A1 | 4/2010 | Biedermann et al. |
| 2010/0087863 A1 | 4/2010 | Biedermann et al. |
| 2010/0087865 A1 | 4/2010 | Biedermann et al. |
| 2010/0088782 A1 | 4/2010 | Moumene et al. |
| 2010/0094348 A1 | 4/2010 | Biedermann et al. |
| 2010/0137912 A1 | 6/2010 | Alcock et al. |
| 2010/0174319 A1 | 7/2010 | Jackson |
| 2010/0198261 A1 | 8/2010 | Trieu et al. |
| 2010/0198269 A1 | 8/2010 | Taylor et al. |
| 2010/0204736 A1 | 8/2010 | Biedermann et al. |
| 2010/0211104 A1 | 8/2010 | Moumene et al. |
| 2010/0211105 A1 | 8/2010 | Moumene et al. |
| 2010/0222819 A1 | 9/2010 | Timm et al. |
| 2010/0228292 A1 | 9/2010 | Arnold et al. |
| 2010/0249843 A1 | 9/2010 | Wegzyn, III |
| 2010/0256682 A1 | 10/2010 | Fallin et al. |
| 2010/0262187 A1 | 10/2010 | Marik et al. |
| 2010/0262190 A1 | 10/2010 | Ballard et al. |
| 2010/0274285 A1 | 10/2010 | Rouleau |
| 2010/0274287 A1 | 10/2010 | Rouleau et al. |
| 2010/0274288 A1 | 10/2010 | Prevost et al. |
| 2010/0331887 A1 | 12/2010 | Jackson et al. |
| 2011/0301644 A1 | 12/2011 | Belliard |
| 2012/0035660 A1 | 2/2012 | Jackson |
| 2012/0053636 A1 | 3/2012 | Schmocker |
| 2012/0221054 A1 | 8/2012 | Jackson |
| 2013/0123853 A1 | 5/2013 | Seme et al. |
| 2013/0197582 A1 | 8/2013 | Prevost et al. |
| 2014/0018857 A1 | 1/2014 | Jackson |
| 2014/0039555 A1 | 2/2014 | Jackson |
| 2014/0222076 A1 | 8/2014 | Jackson |
| 2014/0343610 A1 | 11/2014 | Jackson |
| 2014/0379030 A1 | 12/2014 | Jackson |
| 2015/0216567 A1 | 8/2015 | Trautwein et al. |
| 2015/0230827 A1 | 8/2015 | Zylber et al. |
| 2015/0320449 A1 | 11/2015 | Jackson |
| 2016/0310169 A1 | 10/2016 | Jackson et al. |
| 2016/0310171 A1 | 10/2016 | Jackson |
| 2016/0346010 A1 | 12/2016 | Jackson |
| 2016/0354118 A1 | 12/2016 | Belliard et al. |
| 2016/0354120 A1 | 12/2016 | Jackson |
| 2017/0100165 A1 | 4/2017 | Jackson |
| 2017/0231662 A1 | 8/2017 | Jackson |
| 2017/0340362 A1 | 11/2017 | Jackson |
| 2018/0243008 A1 | 8/2018 | Jackson |
| 2019/0183534 A1 | 6/2019 | Jackson |
| 2019/0231395 A1 | 8/2019 | Jackson |
| 2019/0239925 A1 | 8/2019 | Jackson |
| 2019/0365427 A1 | 8/2019 | Jackson |

FOREIGN PATENT DOCUMENTS

| | | |
|---|---|---|
| DE | 4239716 | 8/1994 |
| DE | 4425392 | 11/1995 |
| DE | 19507141 | 9/1996 |
| DE | 19509141 | 9/1996 |
| DE | 19509331 | 9/1996 |
| DE | 29806553 | 7/1998 |
| DE | 29810798 | 12/1999 |
| DE | 19951145 | 5/2001 |
| DE | 10236691 | 2/2004 |
| DE | 102007055745 | 7/2008 |
| EP | 0667127 | 8/1995 |
| EP | 0669109 | 8/1995 |
| EP | 0677277 | 10/1995 |
| EP | 0885598 | 12/1998 |
| EP | 1121902 | 8/2001 |
| EP | 1190678 | 3/2002 |
| EP | 1570795 | 2/2005 |
| EP | 1570795 | 9/2005 |
| EP | 1579816 | 9/2005 |
| EP | 1634537 | 3/2006 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2846223 | 4/2004 |
| FR | 2857850 | 4/2004 |
| FR | 2865378 | 10/2004 |
| GB | 1519139 | 7/1978 |
| GB | 2365345 | 2/2002 |
| GB | 2382304 | 5/2003 |
| JP | 10277070 | 10/1998 |
| JP | 2000325358 | 3/2000 |

(56) References Cited

FOREIGN PATENT DOCUMENTS

| | | |
|---|---|---|
| SU | 313538 | 10/1971 |
| WO | WO92/03100 | 3/1992 |
| WO | WO94/10927 | 5/1994 |
| WO | WO94/26191 | 11/1994 |
| WO | WO9641582 | 12/1996 |
| WO | WO2001/45576 | 6/2001 |
| WO | WO02/054966 | 7/2002 |
| WO | WO2002/102259 | 12/2002 |
| WO | WO2003/026523 | 4/2003 |
| WO | WO03/068088 | 8/2003 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/055374 | 7/2005 |
| WO | WO2005/065375 | 7/2005 |
| WO | WO2005/072632 | 8/2005 |
| WO | WO2005/082262 | 9/2005 |
| WO | WO2005/099400 | 10/2005 |
| WO | WO2005/104969 | 11/2005 |
| WO | WO2006/005198 | 1/2006 |
| WO | WO2006/012088 | 2/2006 |
| WO | WO2006/017616 | 2/2006 |
| WO | WO2006/020530 | 2/2006 |
| WO | 2006/028537 | 3/2006 |
| WO | WO2006/045094 | 4/2006 |
| WO | WO2006/086537 | 8/2006 |
| WO | WO2006/116662 | 11/2006 |
| WO | WO2006/119241 | 11/2006 |
| WO | WO2007/002409 | 1/2007 |
| WO | WO2007/118045 | 10/2007 |
| WO | WO2007/124222 | 11/2007 |
| WO | WO2007/130835 | 11/2007 |
| WO | WO2007/130840 | 11/2007 |
| WO | WO2007/130941 | 11/2007 |
| WO | WO2008/045210 | 4/2008 |
| WO | WO2008/069420 | 6/2008 |
| WO | WO2008/088990 | 7/2008 |
| WO | WO2008/089075 | 7/2008 |
| WO | WO2008/140756 | 11/2008 |
| WO | WO2009/036541 | 3/2009 |
| WO | WO2010/018316 | 2/2010 |
| WO | WO2010/018317 | 2/2010 |
| WO | WO2010/019704 | 2/2010 |
| WO | WO2010/019857 | 2/2010 |

OTHER PUBLICATIONS

Brochure of Spinal Concepts, an Abbott Laboratories Company, Pathfinder, Minimally Invasive Pedicle Fixation System, Publication Date: Nov. 2003.
Brochure of Spinal Concepts, InCompass, Thoracolumbar Fixation System, Publication Date: Oct. 2003.
Brochure of Spinal Concepts, Pathfinder, Minimally Invasive Pedicle Fixation System, Publication Date: May 2003.
Brochure of Spinal Concepts, Surgical Technique, InCompass, Thoracolumbar Fixation System, Publication Date: Oct. 2003.
Brochure of SpineLine, Current Concepts, Minimally Invasive Posterior Spinal Decompression and Fusion Procedures, Publication Date: Sep./Oct. 2003.
Brochure of Zimmer Spine, Inc., Dynesys® LIS Less Invasive Surgery, The Dynamic Stabilization System, Publication Date: 2005.
*EBI Omega 21* Brochure, EBI Spine Systems, pub. 1999.
*Claris Instrumentation* Brochure, G Med, pub. 1997.
*VLS System Variable Locking Screw* Brochure, Interpore Cross International, 1999.
*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation System* Brochure, Sulzer Medica Spine-Tech, no publish date.
*SDRS Surgical Dynamics Rod System* Brochure, Surgical Dynamics, pub. 1998-99.
*Versalok Low Back Fixation System* Brochure, Wright Medical Technology, Inc., pub. 1997.
*The Strength of Innovation* Advertisement, Blackstone Medical Inc., no publish date.
*The Moss Miami 6. 0mm System* Advertisement, author unknown, no publish date.
*Spine*, Lipcott, Williams & Wilkins, Inc. vol. 24, No. 15, p. 1495.
Brochure of Tyco/Healthcare/Surgical Dynamics on Spiral Radius 90D, Publication Date: Sep. 2001, pp. 1-8.
Overlap. Merriam-Webster. accessed Apr. 13, 2015 http://www.merriam-webster.com/dictionary/overlap.
U.S. Appl. No. 15/883,794, filed Jan. 30, 2018, Jackson.
U.S. Appl. No. 15/918,181, filed Mar. 12, 2018, Jackson.
U.S. Appl. No. 15/852,866, filed Dec. 22, 2017, Jackson et al.
U.S. Appl. No. 15/835,216, filed Dec. 7, 2017, Jackson et al.
U.S. Appl. No. 15/943,257, filed Apr. 2, 2018, Jackson.
U.S. Appl. No. 16/677,981, filed Nov. 8, 2019, Jackson.

\* cited by examiner

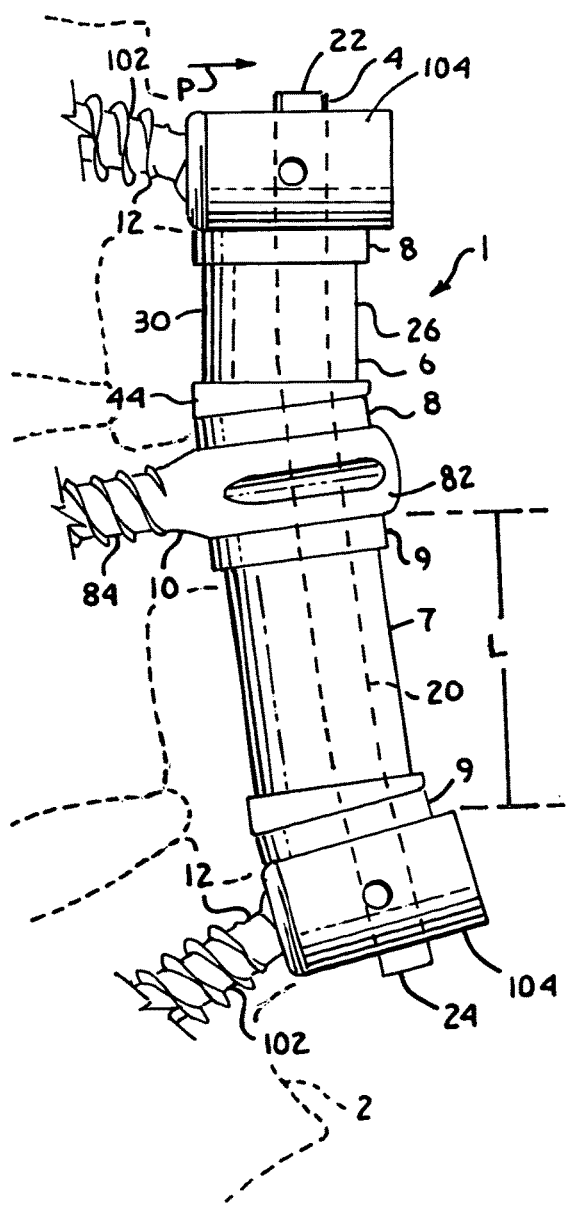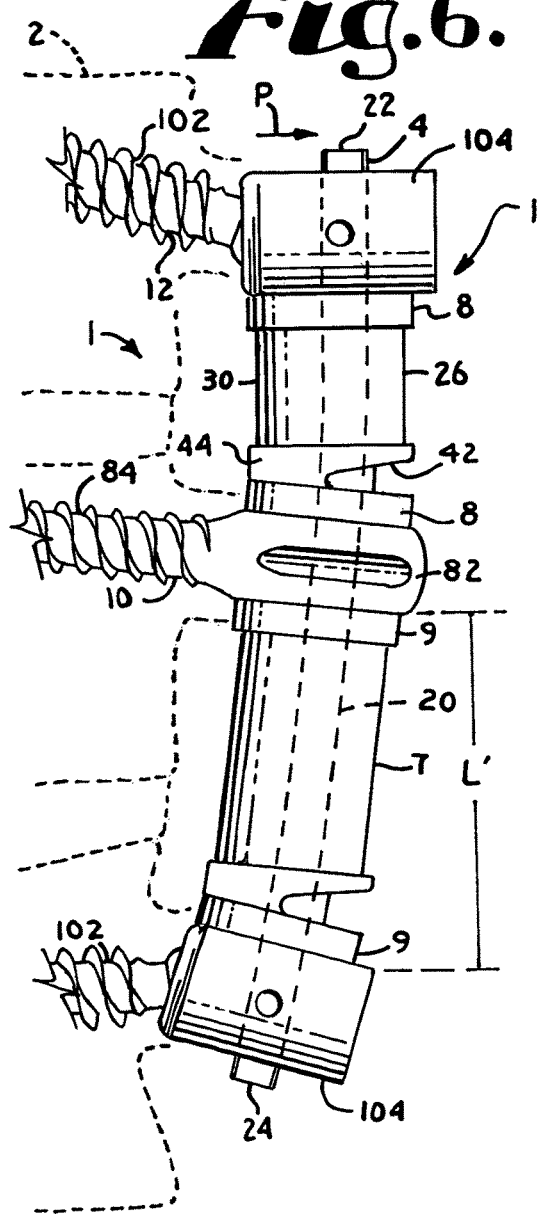

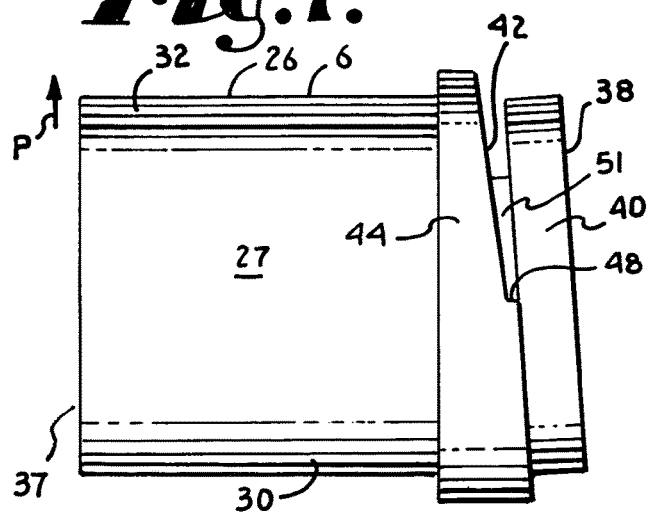
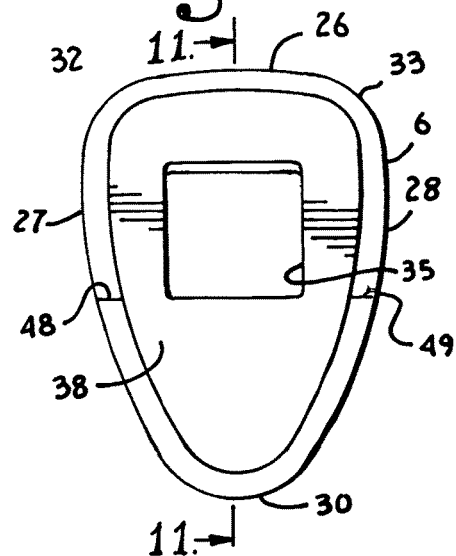
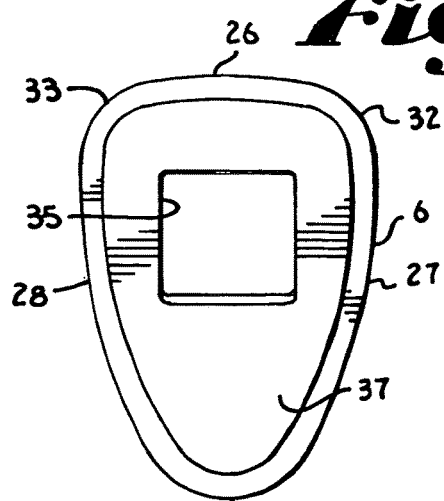
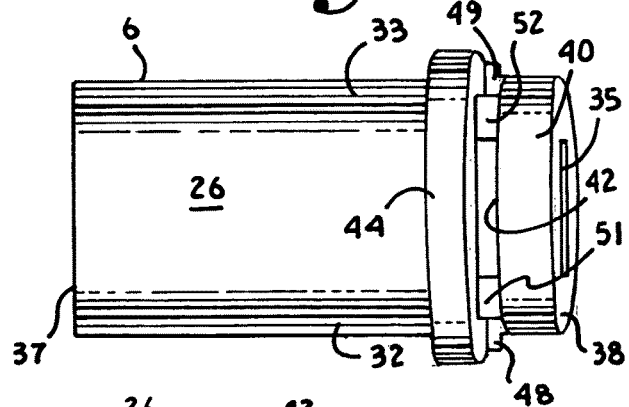
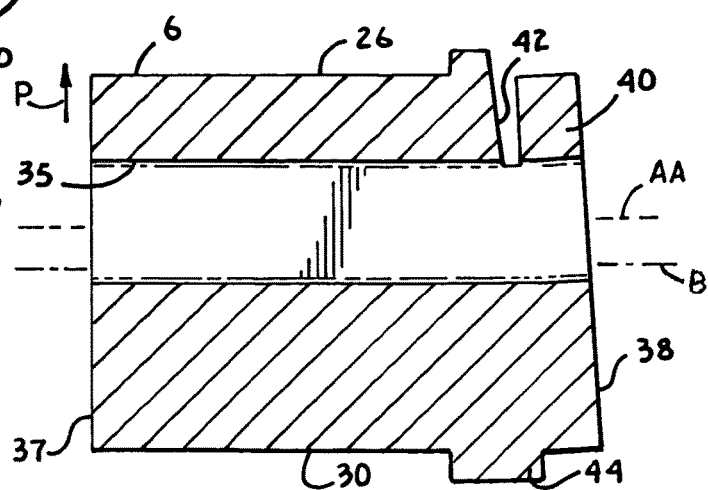

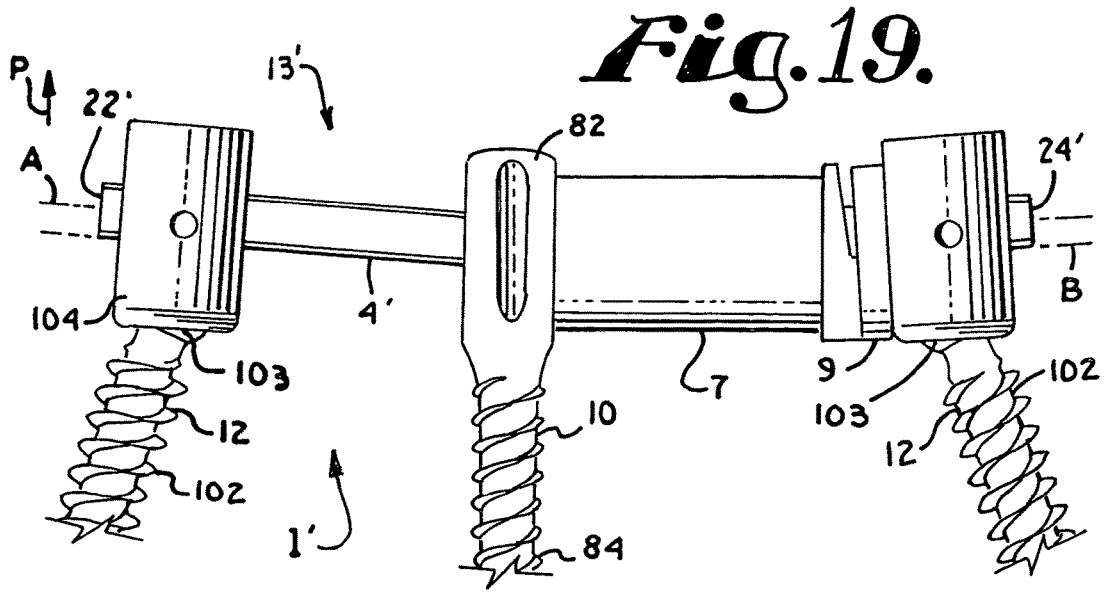
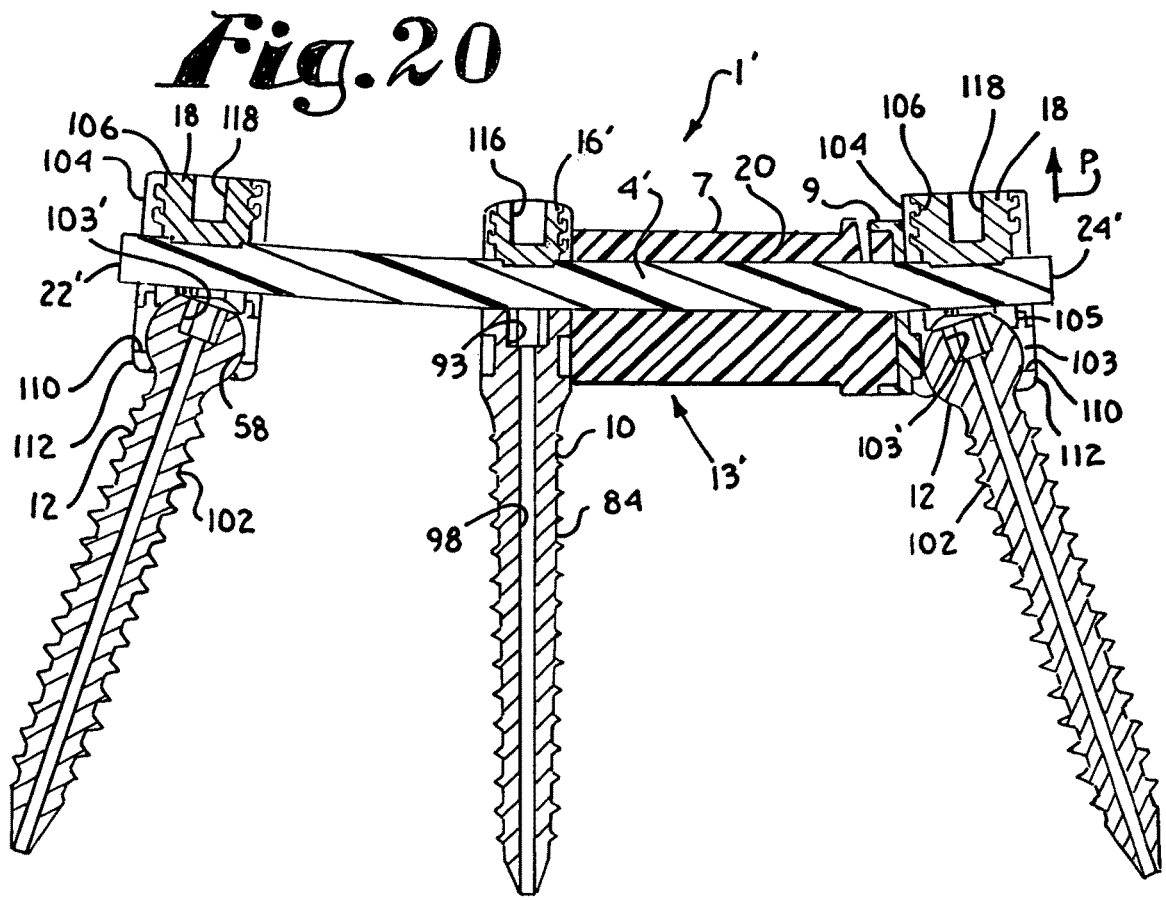

FLEXIBLE SPINAL STABILIZATION ASSEMBLY WITH SPACER HAVING OFF-AXIS CORE MEMBER

CROSS-REFERENCE TO RELATED APPLICATIONS

This application claims the benefit of U.S. Provisional Patent Application Ser. No. 61/192,312, filed Sep. 17, 2008 and U.S. Provisional Patent Application Ser. No. 61/210,058 filed Mar. 13, 2009, both of which are incorporated by reference herein. This application is also a continuation-in-part of U.S. patent application Ser. No. 12/221,442 filed Aug. 1, 2008, that is a continuation-in-part of U.S. patent application Ser. No. 11/328,481 filed Jan. 9, 2006, both of which are incorporated by reference herein. This application is also a continuation-in-part of U.S. patent application Ser. No. 12/069,577 filed Feb. 11, 2008 that claims the benefit of U.S. Provisional Patent Application Ser. Nos. 60/900,816 filed Feb. 12, 2007 and 60/997,079 filed Oct. 1, 2007, all three of which are incorporated by reference herein. This application is also a continuation-in-part of U.S. patent application Ser. No. 11/894,001 filed Aug. 17, 2007 that claims the benefit of U.S. Provisional Patent Application Ser. No. 60/851,353 filed Oct. 12, 2006, both of which are incorporated by reference herein.

BACKGROUND OF THE INVENTION

The present invention relates to apparatuses and methods for use in performing spinal surgery and, in particular, to flexible bone attachment structures or implants for spinal support and alignment that provide variable degrees of segmental stiffness, and therefore flexibility, preferably using minimally or less invasive techniques for insertion of the implants. Due to the different degrees of segmental stiffness, certain embodiments of the apparatus of the present invention can be used with and/or without fusion.

The spine is structured as a repeating sequence of vertebrae, intervertebral discs and facet joints supported and held together by surrounding ligaments and muscles. The vertebra is a block of bone configured as a body anteriorly and laminae, extending posteriorly to form a spinous process, which are connected in the middle by a pair of pedicles. The spine can be divided into motion segments which include two adjacent vertebrae anteriorly, an intervening disc and associated facet joints posteriorly. The spine can be bent, compressed, stretched and twisted. In certain alignments, the spine is fairly shear resistant, but in some alignments it is not shear resistant. The spine is construed as a column which can be divided into three sections: anterior, middle and posterior columns. The anterior column includes the front half of the discs; the middle column includes the back half of the discs, plus the spinal canal and pedicles; and the posterior column includes the facet joints, laminae and spinous processes. The spine is thus a continuation of connected articulated motion segments which can be bent in multiple directions, including flexion and extension. Natural or normal bio-mechanical movement of the spine requires shortening of the posterior column length in extension and elongation or expansion of this length in flexion, with a substantial change in the interpedicular distance.

Historically, it has been common to fuse adjacent vertebrae that are placed in fixed relation by the insertion or installation therealong of bone screws or other bone anchors and cooperating longitudinal connecting members or other elongate members. Fusion results in the permanent and very stiff immobilization of one or more of the spinal motion segment intervertebral joints. Because the anchoring of bone screws, hooks and other types of anchors directly to a vertebra can result in significant forces being placed on the vertebra, and such forces may ultimately over time result in the loosening of the bone screw or other anchor implants from the vertebra due, in part, to the considerable stiffness of such implants, fusion allows for the growth and development of a permanent bone counterpart to the longitudinal connecting member that can maintain the spine in the desired position, even if the implants ultimately fail, fracture, loosen or are removed. However, fusion itself also results in considerable stiffness of the spinal segment being fused with its own associated consequences. Because fusion has been a desired component of spinal stabilization procedures in the past, longitudinal connecting members have been designed that are of a material, size and shape to largely resist flexion, extension, torsion, side bending, distraction and compression, and thus substantially immobilize the portion of the spine that is to be fused. Thus, longitudinal connecting members are typically uniform along an entire length thereof, and usually made from a single or integral piece of material having a uniform diameter, width or cross-sectional area of a size to provide substantially firm rigid support in all planes with little flexibility. Again, fusion often results in too much stiffness for the segment of spine being fused, even if the implants are later removed. This can result in multiple adverse side-effects, including loss of motion and accelerated degenerative changes at junctional levels.

An alternative to fusion, which immobilizes at least a portion of the spine, and the use of more stiff and even rigid longitudinal connecting members or other stiff, rigid and hard structures has been a "soft" or "dynamic" stabilization approach in which a flexible loop-, S-, C- or U-shaped member or a coil-like and/or a spring-like member is utilized as a less stiff longitudinal connecting member with elastic fixed return between a pair of pedicle screws in an attempt to create a flexible stabilization and the possibility for a more normal loading pattern between the vertebrae in flexion, extension, distraction, compression, side bending and torsion. Another type of soft or less stiff system known in the art includes bone anchors connected by limp cords or strands that can be bent and that intrinsically have little to no bending stiffness. Such a cord or strand may be threaded through cannulated spacers that are disposed between adjacent bone anchors when such a cord or strand is implanted, tensioned and attached to the bone anchors, thereby compressing the spacers. The spacers typically span the distance between bone anchors, providing some degree of bending stiffness and limits on the bending movement of the surrounded cord or strand and thus strengthening and supporting the overall system. However, such known systems have provided limited control with respect to torsional and shear forces and little to no allowance for lengthening or increasing distance between the heads or bodies of posteriorly positioned bone anchors with flexion, which is critical for correct spinal bio-mechanics as it relates to flexible stabilization or even to natural segmental spinal motion. Also, such known systems have provided no differentiation between bending stiffness in flexion compared to that in extension (i.e., more stiffness in flexion versus that in extension).

SUMMARY OF THE INVENTION

A flexible stabilization assembly according to the invention includes an elongate inner core member and at least one spacer with elastic flexibility, the spacer surrounding the inner core member. The core member can be pre-tensioned or not, elastic or not and have varying degrees of bending stiffness. If the core member has adequate bending stiffness, the core member does not need to be pre-tensioned, but, in some embodiments, may be pre-tensioned to provide more stiffness and less flexibility. The spacer includes an off-axis lumen or through bore, aperture or opening sized and shaped to closely receive the inner core member which can also have varying degrees of flexibility and which can be inserted within the spacer lumen, and, after implantation, can be slidable or not within the flexible spacer. When implanted, the inner core is posteriorly located with respect to a central axis of the spacer, and, therefore, has a mechanical advantage to compress and flex or bend the spacer more posteriorly than anteriorly when tensioned. In certain embodiments of the invention, the spacer is substantially ovoid in cross-section and may include one or more compression grooves. Furthermore, embodiments of the invention may include none, one or more end caps, covers or sleeves disposed on either side of the spacer and in fixed relation thereto. The optional end cap or caps also include an off-axis through bore with respect to a center or central axis of the cap and are sized and shaped to slidingly receive the inner core. The end cap or caps may also provide a projecting peg-like structure to engage bone anchors. At least a pair of bone anchors cooperate with the elongate core member with the optional end cap engaging the spacer at one end thereof and a bone anchor on the opposite side of the end cap, fixing the spacer to the bone anchors with respect to relative rotation and also being resistant to shear forces, in part, due to the engaging peg-like structure on the end cap and, in some embodiments, on the spacer. The spacers are configured to resist relatively more compression anteriorly and, in cooperation with certain types of core members, allow more compression and/or bending posteriorly and further to provide for an increase in distance posteriorly between opposing bone anchor bodies or heads during certain bending movements of the spinal motion segment, such as flexion, extension and lateral bending. The spacers can be used with two, one or no end caps and at least one end of the spacer can be configured to provide an integral projecting peg-like structure to directly engage the bone anchor. The elastically flexible and compressible spacers can be pre-tensioned, or not and have variable degrees of stiffness in compression and bending. The spacers can make the bending stiffness for the core member stiffer in one direction versus another. The spacer itself can be made from a material that is stiffer in one region versus another (i.e., top to bottom or side to side). In addition, in some embodiments, the off-axis spacer can uniquely urge the spine into extension when compressed axially. In this way, when pre-tensioned, the spacer can provide the possibility for some elastic return to a more extended position for the spinal motion segment which is desirable for the lordotic lumbar spine.

OBJECTS AND ADVANTAGES OF THE INVENTION

An object of certain embodiments of the invention is to provide less stiff and more flexible medical implant stabilization assemblies having longitudinal connecting members that include an elastically flexible portion or section that limits response to torsional and shear forces while allowing for controlled and varied compression axially and in flexion, extension, and lateral bending of the assembly as well as elongation or distraction with lateral bending and flexion between the body or head of bone anchors positioned posteriorly. A further object of certain embodiments of the invention is to provide such an implant wherein the flexible member portion or section includes an elastically flexible spacer and an inner core that may be flexible, with no to some degree of elasticity, and, in some embodiments, may have no up to a considerable degree of bending stiffness. Another object of certain embodiments of the invention is to provide such an implant wherein the inner core is received by a flexible spacer having an off-axis lumen, the core being located in a posterior location with respect to a remainder of the spacer when the spacer is implanted along a human spine between two bone anchors, the bendable core member being pre-tensioned or not, and in certain embodiments wherein the core member has little to no significant degree of bending stiffness, the core member being tensioned at the time of insertion. An important object for some embodiments of the invention having the unique off-axis spacer design, is that, when it is compressed, the spacer provides and creates a fulcrum for cantilevered extension of the spinal motion segment when utilized with the cooperating bone screw shanks; this being desirable in that it better off-loads and protects the disc, especially the back half of the disc, and the associated facet joints. A further object of certain embodiments of the invention is to provide flexible medical implant longitudinal connecting members that may be utilized with a variety of bone screws, as well as hooks and other bone anchors. Additionally, it is an object of certain embodiments of the invention to provide a lightweight, reduced volume, low profile assembly including at least two bone anchors and a longitudinal connecting member therebetween featuring a spacer that resists compression anteriorly and allows varying degrees of compression and expansion posteriorly, making the device stiffer to bend in one direction versus another. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 5 is an enlarged and partial side elevational view, similar to FIG. 2, showing the assembly of FIG. 1 responding to a combination of spinal extension and flexible spacer compression, with portions of a human spine shown in phantom.

FIG. 6 is an enlarged and partial side elevational view, similar to FIG. 2, showing the assembly of FIG. 1 responding to a combination of spinal flexion and tension with anterior spacer compression and posterior spacer elongation or expansion, with portions of a human spine shown in phantom.

FIG. 7 is an enlarged side elevational view of one of the spacers of the assembly of FIG. 1.

FIG. 8 is an enlarged rear elevational view of the spacer of FIG. 7.

FIG. 9 is an enlarged, front elevational view of the spacer of FIG. 7.

FIG. 10 is an enlarged top plan view of the spacer of FIG. 7.

FIG. 11 is a cross-sectional view taken along the line 11-11 of FIG. 9.

FIG. 19 is an enlarged and partial side elevational view of an alternative embodiment of a flexible stabilization assembly and cooperating bone screws according to the invention.

FIG. 20 is another enlarged side elevational view of the assembly and bone screws of FIG. 19 with portions broken away to show the detail thereof.

DETAILED DESCRIPTION OF THE INVENTION

Figure 1:
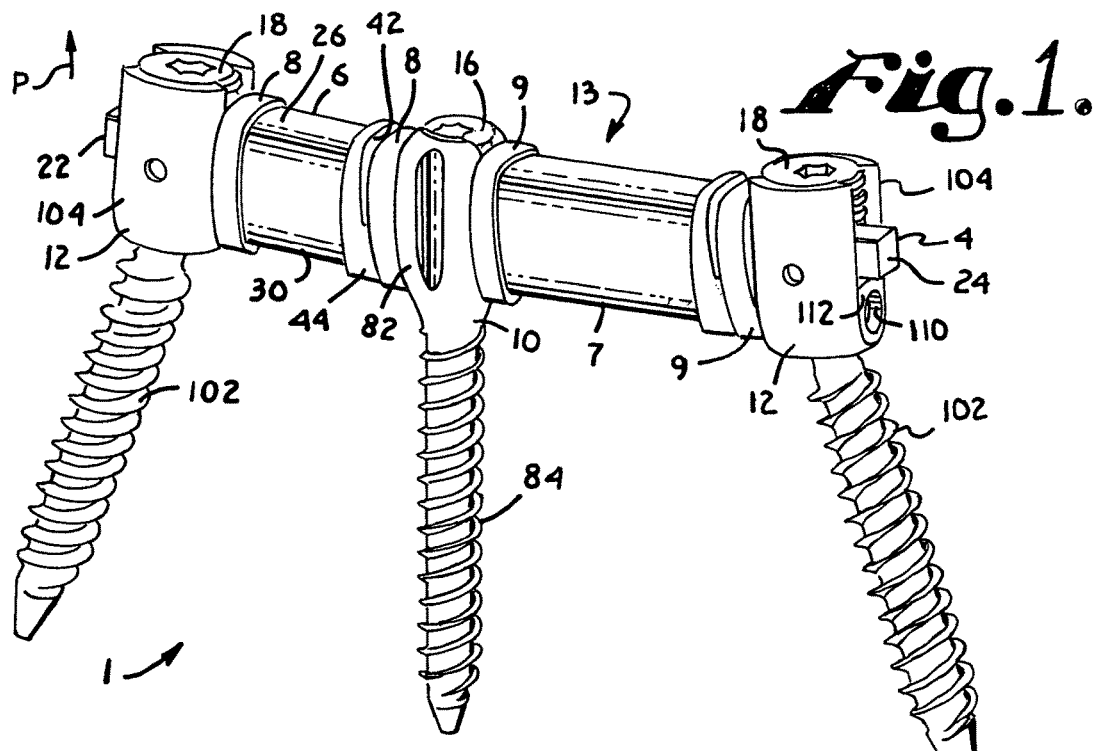
FIG. 1 is an enlarged perspective view of a flexible stabilization assembly of the invention having an inner flexible core, a pair of outer flexible spacers, an optional pair of stiffer end caps cooperating with each spacer and further shown cooperating with one monoaxial bone screw and two polyaxial bone screws of the invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

Different materials can be used to support the complicated bio-mechanical structure of the spine, and thus spinal implants of the invention may employ a variety of materials including, metals, metal alloys and non-metals, and combinations thereof, exhibiting a wide range of physical characteristics that can be overlapping, inter-related and that may be highly dependent on the geometry into which they are configured. For example, "bendable" and "materials that can be bent" are general terms that lack much specificity, as are the terms rigid, hard, stiff and soft. Bending or yielding can mean ductile with no spring back, or flexible with at least some degree of return to the original shape when the applied force is removed. Most all materials exhibit at least some degree of flexibility, however small, even if materials are otherwise identified as stiff, rigid and/or hard. The degree of flexibility is often referred to as bending stiffness which can range from very low (i.e., soft, limp and therefore no stiffness and no flexibility) to very high. Flexibility is greatly influenced by geometry, for example, the size, shape, length, etc. of a particular structure. Cords, cables strands, straps, etc. can be described as structures that can be bent and have no to low bending stiffness. Such structures and materials generally require pre-tensioning and cooperation with other surrounding and supporting structures to work in the spine. Soft, non-metal elongate structures can have moderate degrees of bending stiffness, such as pure polyetheretherketone (PEEK) rods, but again, the amount of bending stiffness can very greatly. Metal elongate structures typically exhibit higher bending stiffness, but not always, and while such structures can be tensioned and compressed, they generally do not alter their geometry in the direction of tension or compression (i.e., such structures are typically not compressible and stretchable). Materials used on the spine which have at least some degree of bending stiffness are generally expected to function in a range below a yield strength thereof.

Some materials utilized for spinal stabilization according to the invention exhibit elasticity. Elastic behavior implies flexibility plus compressibility, stretchability and even the ability to be twisted with complete or near complete elastic return to an original shape of such material with little permanent deformation in the material itself. Elasticity is a more specific type of flexibility and a metal spring or a rubber band are good structural examples of elastic behavior which can also have very low to no bending stiffness. Materials utilized in some embodiments of the invention can also exhibit viscoelastic behavior, which implies creep with some degree of permanent deformation over time. When the deforming force is stopped or released, the material deformation may recover somewhat. Again, such materials can be identified as flexible. Viscoelastic materials, in addition to being flexible, can have different degrees of stiffness in compression and tension and may be more or less hard (rigid) or soft, for example.

Flexible spinal stabilization assemblies according to the invention utilize different materials having the aforementioned physical characteristics to support and complement the complicated bio-mechanics of the spine. In particular, a focus of certain embodiments of the present invention is a unique flexible spacer working in conjunction with an off-axis core member. The core member can have high to low or no bending stiffness. The core member can also exhibit elastic as well as viscoelastic behavior. The core member may or may not be pre-tensioned.

With particular reference to FIGS. 1-18, the reference numeral 1 generally designates a less stiff flexible stabilization assembly of the invention that is durable enough to be used on a spine 2 (in phantom in FIGS. 5 and 6) with and/or without fusion. The illustrated assembly 1 includes the following components: an elongate flexible core, illustrated as a bar 4; at least one cannulated spacer 6 and illustrated with a second cannulated spacer 7; a pair of optional anti-torque/anti-shear sleeves or end caps 8 located on either side of the spacer 6; a second pair of optional anti-shear end-caps 9 located on either side of the spacer 7; a monoaxial bone screw 10 with optional anti-rotation and anti-shear end-cap receiving structure; and a pair of polyaxial bone screws 12, each having optional anti-rotation and anti-shear end-cap receiving structure. The elongate inner core 4 is slidingly receivable within the spacers 6 and 7, and end-cap pairs 8 and 9 to form a connecting member, generally 13, that is eventually captured by and may be fixed to each of the three bone screws 10, 12. In the illustrated embodiment, the core 4 is captured and slidingly received by the bone screw 10 while the core 4 is captured by and fixed in position with respect to the screws 12. Each of the end cap pairs 8 and 9 engages respective spacers 6 and 7 on one side thereof and a bone screw 10 or 12 on an opposed side thereof. As will be described in greater detail below, when fully assembled and all the components are located or fixed in position as shown in FIGS. 1-6, for example, the core 4 is implanted in a neutral state (e.g., if it has adequate bending stiffness) or in tension (e.g., if it is a limp, cord-like or cable-like structure) and the spacers 6 and 7 may be in compression or in a neutral state, the core 4 and spacers 6 and 7 combination providing for modified protected spinal movement in spinal flexion and extension, for example, with the cooperating end cap pairs engaging the screws to help to control shear and torsion. Even if the core member has adequate bending stiffness, the core member can still be pre-loaded in tension, thereby compressing the spacers. Furthermore, the off-axis location of the lumen running through the spacers 6 and 7 places the core 4 and the spacer lumen in an advantageous posterior position with respect to the spacers and their centers, allowing for greater compression of posterior (posterior direction indicated by an arrow P in the drawing figures) portions of the spacers during pre-tensioning, if any, and during spinal extension. In this way, greater potential spinal extension can occur, as well as greater spread or separation between bone screw heads or receivers during spinal flexion, than would be possible otherwise with a spacer having a more central or on-axis lumen. With certain types of flexible core members, during spinal flexion, when the core 4 is disposed in the posteriorly located off-axis lumen of each of the spacers, the anterior portions of the spacers act as a fulcrum, advantageously increasing spread between the bone screw heads due to the unique design of the flexible spacers 6 and 7. During certain spinal movements, the off-axis spacers advantageously transfer an operative axis of segmental rotation of the device 13 anterior to neighboring facet joints, guarding against overload of such joints in compression, especially with flexion.

Figure 2:
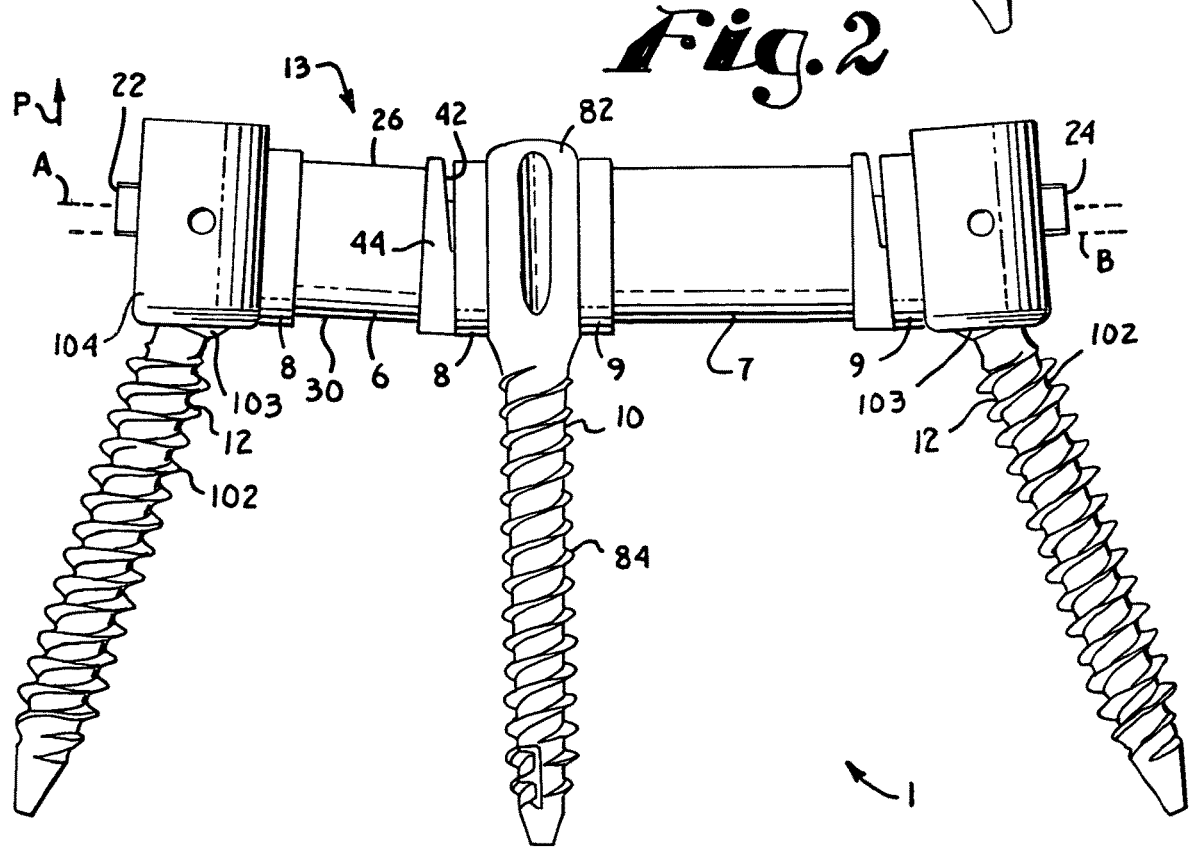
FIG. 2 is an enlarged side elevational view of the assembly and bone screws of FIG. 1.
Figure 3:
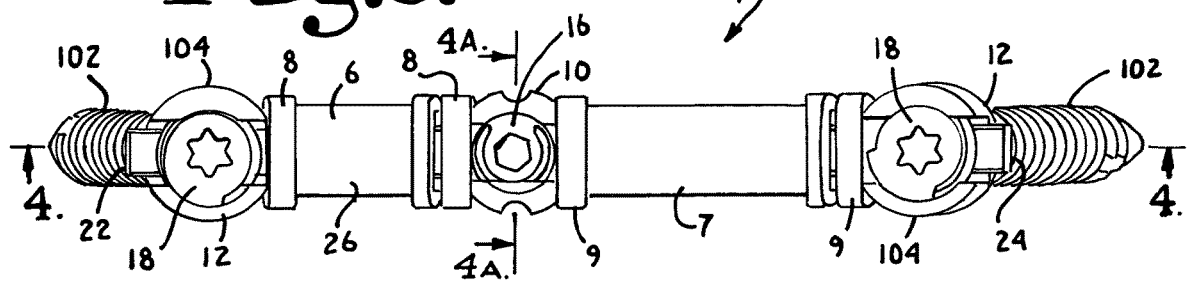
FIG. 3 is an enlarged top plan view of the assembly and bone screws of FIG. 1.

As illustrated, for example, in FIGS. 1-3, the flexible connecting member assembly 1 includes at least two bone anchors and is illustrated with one fixed or monoaxial screw 10 cooperating with a closure 16 (or a closure 16') and two polyaxial screws 12 each cooperating with a closure 18, the assembly 13 being captured and fixed in place at portions of the core 4 located on either side of the spacers 6 and 7 and between the spacers 6 and 7. Although the screws 10 and 12 are illustrated, it is noted that the assembly 1 may be used with two or more screws 10 or two or more screws 12 or any combination of the screws 10 and 12. Furthermore, in addition to the monoaxial and polyaxial bone screws shown in the drawing figures, a variety of bone screws and other bone anchors may be modified to include surfaces for cooperation with the core 4 and the optional end caps 8 and 9, including hinged bone screws, other types of polyaxial bone screws, and bone hooks and the like, with or without compression inserts, that may in turn cooperate with a variety of closure structures having threads, flanges, or other structure for fixing the closure structure to the bone anchor, and may include other features, for example, external or internal drives, break-off tops and inner set screws. The closures can be configured for locking and sliding on the core or locking and fixing the core. The bone anchors, closure structures and the connecting member 13 are then operably incorporated in an overall spinal implant system for correcting degenerative conditions, deformities, injuries, or defects to the spinal column of a patient.

The connecting member 13 is elongate, with the inner core 4 being any flexible elongate material extending substantially along a longitudinal axis A (when in a neutral state), the form of the flexible core 4 including, but not limited to elastic, inelastic and/or deformable bars of rectangular, oval, square or circular cross-section, as well as other curved and polygonal cross-section shapes. The core 4 may be made from a variety of elastic and inelastic materials, deformable or not in compression and tension. The core can have little to no bending stiffness or substantial bending stiffness. The core materials include, but are not limited to natural or synthetic elastomers such as polyisoprene (natural rubber), and synthetic polymers, copolymers, and thermoplastic elastomers, for example, polyurethane elastomers such as polycarbonate-urethane elastomers. The core 4 can be made of metal as well as non-metal materials and can be in the structure of a non-metal limp-like cord and a metal limp cable, both of which would require pre-tensioning in use. The core 4 may further be made from polymers such as polyetheretherketone (PEEK) or ultra-high-molecular weight-polyethylene (UHMWP). The core 4 can be made of solid material or the core 4 can be a composite. A preferred core 4 of the invention is of non-circular cross-section as such design aids in torsion and shear control of the connecting member 13. Flexible core members made of solid or composite materials generally provide some degree of bending stiffness and can be used with and without pre-tensioning, especially if made of PEEK. The core 4 may be a cord, cords, threads, strings, straps, bands, cables or fibers that may be single or multiple strands, including twisted, woven, braided or plaited materials that may be of circular or other cross-sections. Again, such core members generally have no bending stiffness and require pre-tensioning in use. In addition to the bending elastomeric materials identified above, cores in the form of a cord, cable, strand, band, or the like may be made from a variety of materials, including polyester or other plastic fibers, strands or threads, such as polyethylene-terephthalate. It is foreseen that the core 4 could be made of absorbable materials.

The illustrated core 4 has a substantially uniform elongate body 20 of substantially rectangular or square cross-section, a first end 22 and an opposed second end 24, the core 4 being cut to length as required by the surgeon. The core 4 can also be connected or clamped to a rod on one end to form a hybrid construct. Initially, the core 4 may be of a length longer than shown in the drawings to allow for gripping of the core 4 during assembly with the other components of the connecting member 13 and also for tensioning with a tool or device (not shown), if needed or desired, and attachment to the bone screws of the assembly 1. The core 4 may be placed under axial tension prior to installation between the bone screws 10 and 12, for example by being tensioned along the axis A for a selected time to lengthen and otherwise deform the core 4 during a primary creep stage. After the core 4 reaches a secondary or steady-state creep, further tension may then be placed on the core 4 in preparation for fixing to the bone screws 10 and 12. It is noted that the core 4 of the invention may be made from a polymer, such as polyester or polyethylene, that typically does not illustrate substantial elastic properties, such as any significant additional axial distraction, after initial tensioning and assembly within the human body. However, a preferred core 4 of the invention is shown in the form of a stiffer, but flexible elastic bar that may be implanted in a neutral or tensioned state and then be able to extend a significant distance during use due to the elasticity of the core material.

The spacer 6 and the spacer 7 are identical or substantially similar, with the only difference being that they may be of different lengths along a longitudinal axis B as illustrated, for example, in FIG. 2. In use, the spacers can be cut to length on one end by the surgeon. Therefore, only the spacer 6 will be described in detail herein with all attributes of the spacer 6 also applying to the spacer 7. With particular reference to FIGS. 7-11, the spacer 6 is sized and shaped to be closely slidingly received over the core 4 and, in some cases, within portions of the end caps 8. The spacer 6 may be made from a variety of flexible materials, including, but not limited to natural or synthetic elastomers such as polyisoprene (natural rubber), and synthetic polymers, copolymers, and thermoplastic elastomers, for example, polyurethane elastomers such as polycarbonate-urethane elastomers. In order to have low or no wear debris, one or more of the spacer 6 surfaces may be coated with an ultra thin, ultra hard, ultra slick and ultra smooth coating, such as may be obtained from ion bonding techniques and/or other gas or chemical treatments. It is foreseen that the spacer lumen could have a lining extending a partial length thereof, such lining being made of a material different than that of the spacer.

As best shown by FIGS. 8 and 9, the illustrated spacer 6 is substantially ovoid, tear drop or egg-shaped in cross-section, taken perpendicular to the axis B. However, the spacer can be of any suitable cross-sectional shape and size. Another way of describing the spacer 6 geometry cross-section shape is that it can be an isosceles triangle, wherein the corners or vertices are rounded. For example, the spacer 6 includes a first or operatively posterior side or surface 26 and a pair of opposed sides 27 and 28 that are of substantially equal length and converge at the rounded off corner or vertex 30. The side or surface 26 partially defines a posterior region of the spacer 6 and the area near the vertex 30 partially defines an anterior region of the spacer 6. Thus, the corner 30 is implanted in an anterior position with respect to the first or posterior side or surface 26. In clinical use, the anterior corner 30 can be at the level of or anterior to the facet joint. Two other vertices or corners 32 and 33, respectively, are located on either side of the surface 26 are also rounded. Furthermore, rather than being planar, the sides 26, 27 and 28 can also be slightly curved. Thus, the spacer 6 cross-sectional geometry may be best described as a hybrid between a triangle and an egg or ovoid shape. Again, it is noted that the spacer 6 may be of other cross-sectional shapes including triangular, elliptical, oval, rectangular and other polygonal or curved shaped, preferably wherein a maximum height of the spacer 6 measured generally from a posterior to an anterior direction (when implanted) and substantially perpendicular to a length measured between bone screws is greater than a maximum width measured perpendicular to the height and also substantially perpendicular to the spacer length. However, it is foreseen that the spacer could be substantially round and that the lumen could be eccentrically positioned within the spacer.

Figure 4:
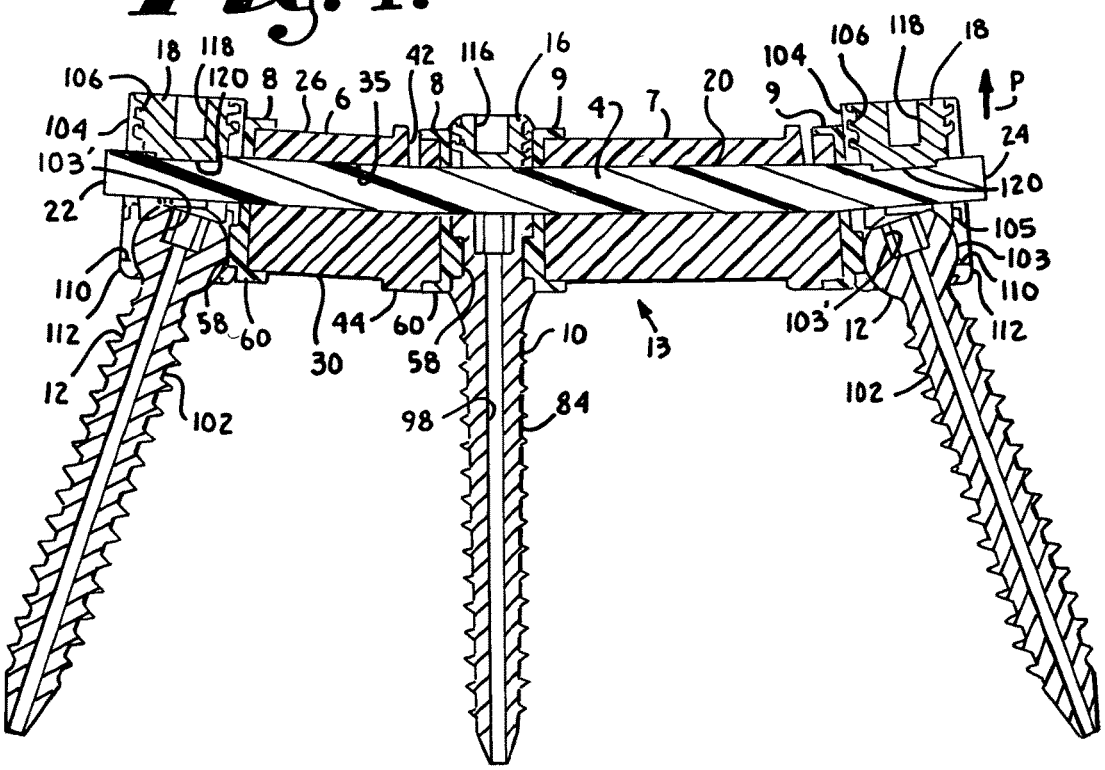
FIG. 4 is an enlarged cross-sectional view taken along the line 4-4 of FIG. 3.

With particular reference to FIGS. 8, 9 and 11, the spacer 6 includes an off-axis through-bore or lumen 35 having a substantially rectangular cross-section oriented substantially perpendicular to the axis B and sized and shaped to closely, slidingly receive the core 4. In the embodiment shown, the non-circular geometry of the core 4 and spacer 6 combination prohibit rotation of the spacer 6 about the core 4 and provide operative torsional resistance for the assembly 1. However, an off-axis round lumen and core could also be used. The lumen 35 extends through the spacer from an end 37 through an apposed end 38. As best illustrated in FIGS. 4 and 11, the lumen 35 is disposed closer to the posterior surface 26 than the rounded vertex 30 and is thus off-axis in position, being centered about an axis AA that is spaced from and substantially parallel to the axis B, with a larger portion and, therefore, volume of the spacer 6 body being located anteriorly of the lumen 35 when the spacer 6 is assembled and implanted with the other assembly components. Each of the opposed ends 37 and 38 are substantially planar. The ends 38 and 38 need not be parallel, but rather can merge slightly toward one another as the end surfaces 37 and 38 run toward the posterior surface 26. The end surface 37 runs substantially perpendicular to the posterior surface 26 and the rounded vertex 30 while the end surface 38 is disposed at an obtuse angle with respect to the surface 26. The lumen 35 runs substantially perpendicular to both end surfaces 37 and 38 and thus curves slightly in a posterior direction towards the surface 26 near the end surface 38. The surface 38 further partially defines an end portion 40 of the spacer 6 that, in this embodiment, is sized and shaped to fit within an end-cap 8 and is disposed adjacent to a groove 42 and a support rim 44. The groove 42 is V-shaped and extends through the posterior surface 26 and into the lumen 35; however, the groove can have different shapes. The groove 42 is generally located between the end portion 40 and the support rim 44, being formed primarily out of the rim 44 that surrounds the posterior surface 26 and each of the side surfaces 27 and 28. The groove terminates at ledges 48 and 49 of the rim 44 located about respective side surfaces 27 and 28 and about midway between the posterior surface 26 and the rounded vertex 30. However, the groove could extend more or less anteriorly in some embodiments. The groove 42 does not cut completely through the lumen 35, but rather is defined, in part, by relatively thin walls 51 and 52 that define the lumen 35 on one side thereof and the groove 42 on an opposed side thereof. In the embodiment shown, the support rim 44 is sized and shaped to fully abut against an end cap 8, as will be described in greater detail below. The rim 44 also provides anterior support for the spacer 6, making the spacer 6 less flexible and compressible near the rounded vertex 30 than at the groove 42 located near the posterior surface 26. It is noted that according to the invention, an off-axis, posteriorly biased lumen may be sufficient to provide a desired posterior spacer portion having less stiffness and greater bending in extension than a thicker anterior portion of such a spacer that would not allow as much bending in flexion. Therefore, spacers of the invention may include one, none or more than one groove, depending upon a desired amount of stiffness with compressibility, flexibility and elasticity selected for a particular embodiment. As discussed above, the spacer 7 differs from the spacer 6 only in length on the end opposite the groove. Both illustrated spacers 6 and 7 include the flexion and extension-compression groove 42 near one end thereof. At the opposite end, for example, at the end 37, the spacer 6 may be cut to length at the factory or by the surgeon, to create a spacer that custom fits between bone screws. The groove 42 is preferably a factory molded feature, but may also be machined.

Figure 27:
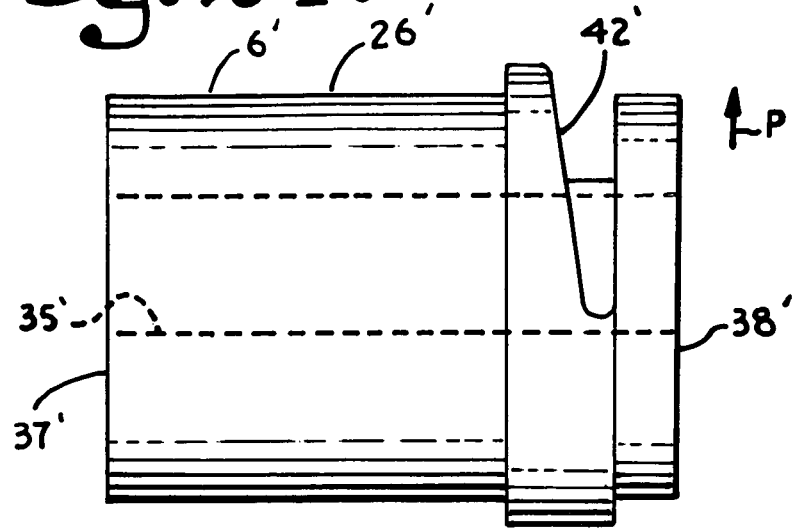
FIG. 27 is an enlarged side elevational view of an alternative spacer according to the invention shown in a neutral position.
Figure 28:
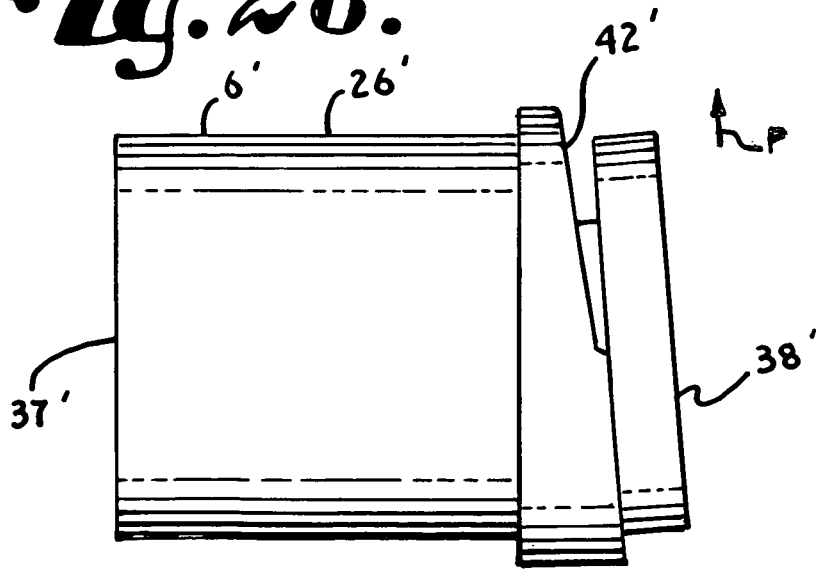
FIG. 28 is an enlarged side elevational view of the spacer of FIG. 27 shown compressed with elastic deformation of the flexible spacer posteriorly and little to no deformation anteriorly.

It is noted that spacers of the invention are also not limited to the particular spacer 6 that has an end surfaces 38 that converges toward the end surface 37 in a direction running towards the posterior surface 26 with the surface 37 being perpendicular to the surface 26. With reference to FIGS. 27 and 28, an alternative embodiment of a spacer 6' of the invention having a lumen 35' is shown that is identical to the spacer 6 with the exception that the spacer 6' includes end surfaces 37' and 38' that are parallel when in a neutral state, both surfaces being perpendicular to a posterior surface 26' and the lumen being parallel with the surface 26'. FIG. 28 illustrates the spacer 6' when in a compressed state wherein the surface 38' angles toward the surface 37' when the spacer 6' compresses at a groove 42'. Spacers of the invention may also include end surfaces that diverge from one another in a posterior direction when in a neutral state.

Figure 29:
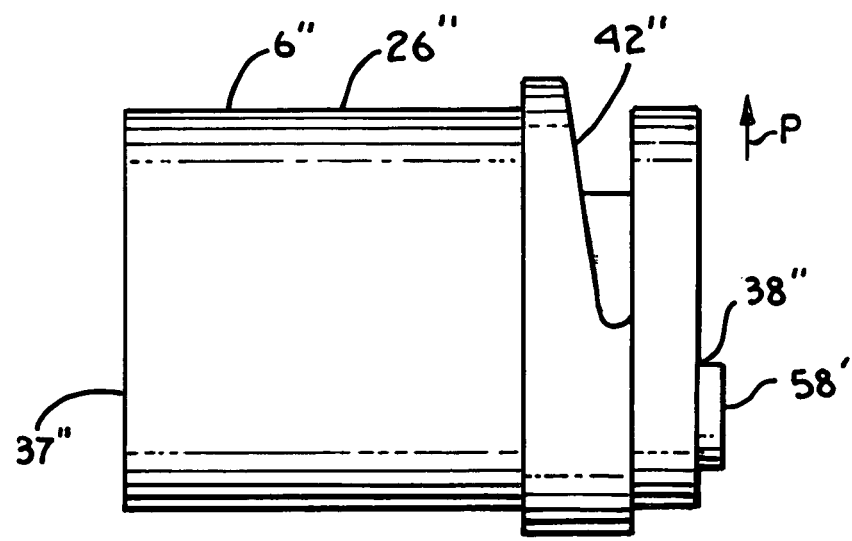
FIG. 29 is an enlarged side elevational view an another alternative spacer according to the invention shown in a neutral position and having a peg extension.

With reference to FIG. 29 another spacer 6" according to the invention is shown that is substantially identical to the spacer 6', having a posterior surface 26", parallel end surfaces 37" and 38", a groove 42" and all other features that are identical or substantially similar in form and function to the respective surface 26', end surfaces 37' and 38', groove 42' and other features of the spacer 6'. Additionally, the spacer 61" includes a bone anchor attachment knob or peg 58' that is the same or substantially similar in form and function to a knob 58 of an end cap or sleeve 8 described in greater detail below. The knob or peg 58' extends from the surface 38" and is sized and shaped to be received in an aperture of the bone screw 10 or 12 when an end cap or sleeve 8 is not used in the assembly of the invention, as will be described in greater detail below with respect to FIG. 31.

With particular reference to FIGS. 12-15, the alternative end cap or sleeve 8 is shown. The illustrated end caps 9 are identical to the end caps 8, therefore, only one end cap 8 will be described herein. Each end cap 8 is sized and shaped to closely receive the end portion 40 at the surface 38 of the spacer 6 or an opposite end portion of the spacer 6 at the surface 37. Each cap 8 includes an outer planar surface 55 and an opposed inner planar surface 56. Extending from the outer surface 55 is a bone anchor attachment knob or peg 58 and extending from the inner surface is an integral curved sleeve 60 that has a geometry similar to and slightly larger than the spacer ovoid cross-sectional geometry so as to closely receive the spacer 6 about the surfaces 26, 27 and 28. Thus the sleeve 60 further includes a posterior portion 66, converging side portions 67 and 68, a rounded anterior vertex 70 and rounded vertices 72 and 73 located on either side of the posterior surface 66. An inner sleeve surface 74 is formed by the portions 66, 67, 68, 70, 72 and 73 and extends from the inner planar surface 56 with the surface 56 and surface 74 being in frictional engagement with the spacer 6 at either end thereof during operation. The illustrated sleeve 60 is sized to fit about the spacer portion 40 and abut against the support rim 44 located adjacent to the anterior vertex 30 and portions of the surfaces 27 and 28 located anterior to the groove 42. In other embodiments of the invention that do not have a groove 42 or a support rim 44, the sleeve 60 is sized and shaped to slip over and receive a portion of an end of a spacer, similar to how the sleeve 60 cooperates with the spacer 6 at the end surface 37 thereof. Each end cap 8 further includes a bore 75 of square or rectangular cross-section, having a similar geometry and being positioned to cooperate with the bore 35 of the spacer 6 to provide a path for the core 4 and to closely receive the core 4 therethrough. The knob or peg 58 is sized and shaped to be closely received by an aperture of the bone screws 10 and 12 as will be discussed in greater detail below. The illustrated peg 58 is in the form of a cylinder having an outer surface 50 with a circular cross-section. The peg 58 and corresponding receiving apertures of the bone screws 10 and 12 may be of a variety of geometries that allow for engagement between the end caps 8 and 9 and the bone screws 10 and 12, including but not limited to one or more curved shapes, such as cylindrical and other curved shapes, polygonal shapes having three or more sides and shapes having both curved and planar sides, including ridges and grooves.

The anti-shear end caps 8 and 9 may be made from non-metal and metal or metal alloys, including, but not limited to, titanium, titanium alloys, stainless steel, cobalt chrome, or other suitable materials, including plastic polymers such as polyetheretherketone (PEEK), ultra-high-molecular weight-polyethylene (UHMWP), polyurethanes and composites, including composites containing carbon fiber. It is noted that the end caps 8 and 9 are preferably made from a different material than the bone screws 10 and 12, for example, titanium bone screws advantageously cooperate with caps 8 and 9 made from PEEK. In order to have low or no wear debris, the end cap surfaces and/or engaging, cooperating bone screw 10 and 12 surfaces may be coated with an ultra thin, ultra hard, ultra slick and ultra smooth coating, such as may be obtained from ion bonding techniques and/or other gas or chemical treatments. It is noted that spacers 6 of the invention may be used with or without end caps 8 and that the spacers can also have their own pegs for screw engagement (as shown in FIG. 29). In such embodiments the spacer 6 extends between and engages a pair of bone screws or other bone anchors. Again, the spacers can also have ends with peg-like projections 58' to engage the anchors.

With particular reference to FIGS. 1-3 and 16-18, the bone screw 10 with cooperating closure 16 is a monoaxial screw having an upper core receiving portion 82 integral with a threaded bone attachment portion or shank 84. The portion 82 further includes an open through channel 86 for closely receiving the core 4 therethrough. A portion of the channel 86 is defined by a guide and advancement structure 88 for receiving and mating with the closure 16. The structure 88 includes a run-out aperture or groove partially defined by a bottom or lower seating surface 89 sized and shaped for frictional engagement with a portion of the closure 16, as will be described in greater detail below with respect to FIGS. 4A and 4B. For cooperation with the core 4 that includes parallel planar surfaces, the illustrated channel 86 also includes spaced parallel planar surfaces 90 for closely receiving the core 4 located adjacent the run-out lower surface 89. Also defining the channel 86 is a planar seating surface 91 disposed substantially perpendicular to the pair of spaced surfaces 90. It is noted that the planar surfaces 90 and 91 in cooperation with the closure 16 may also be used to secure a core of circular or other cross-section. Furthermore, bone screws of the invention may have a U-shaped or saddle-shaped bottom seating surface in lieu of the planar surface 91 for receiving a core of circular or other curved cross-section. Formed in the surface 91 is an internal drive aperture 93 for mating with a driving tool to rotate and drive the shank 84 into a vertebra.

The upper, receiving portion 82 further includes opposed, substantially parallel outer side surfaces 92. However, it is foreseen that according to the invention, other embodiments of the invention may include side surfaces 92 that angle away or towards one another for lordosing or kyphosing controlling embodiments as previously described in applicant's application U.S. Ser. No. 11/328,481, incorporated by reference herein. Formed in each of the surfaces 92 is an aperture 94 sized and shaped to closely receive the peg 58 of an end cap 8 or 9 and/or the peg 58' of the spacer 6" or other spacer of the invention modified to include such a peg 58'. In the illustrated embodiment, the apertures 94 are each defined by a cylindrical inner surface 95 and a circular planar surface 96. The surface 95 is sized and shaped to closely receive and frictionally engage the outer cylindrical surface 59 of the knob or peg 58 of the end cap 8 (or 9). The illustrated bone screw 10 is cannulated, having a through bore 98 extending through the shank 84 for receiving a guide wire or pin (not shown) inserted therethrough to provide a guide for the placement and angle of the shank 84 within a vertebra.

With particular reference to FIGS. 1 and 4, the bone screws 12 with cooperating closure tops 18 are open polyaxial screws, each screw generally including a bone screw shank 102 having an upper portion 103 and an internal drive feature 103' in the form of an aperture for example, hex-shaped, for cooperating with a driving tool for rotating and driving the shank 102 in a vertebra (not shown). Each screw 12 also includes a receiver 104 for slidingly pivotally receiving the upper portion 103, and a lower pressure insert 105 having surfaces for engaging the shank upper portion 103 and surfaces for closely receiving the core 4. The bone screw 12 is substantially similar to the polyaxial screw described in Applicant's U.S. patent application Ser. No. 12/229,207, filed Aug. 20, 2008 entitled "Polyaxial Bone Anchor Assembly With One-Piece Closure, Pressure Insert and Plastic Elongate Member," the disclosure of which is incorporated by reference herein (hereafter referred to as the '207 patent application). The screws 12 differ from the screws described in the '207 patent application only in that the screws 12 include a pair of opposed end-cap receiving apertures 110 formed in side surfaces 112 of the receiver 104, the apertures 110 being identical or substantially similar to the apertures 94 of the screw 10.

With reference to FIGS. 1 and 2, the closure structures 16 and 18 may be any of a variety of different types of closure structures for use in conjunction with the present invention with suitable mating structure on the interior surfaces of the respective screws 10 and 12. The illustrated closure structures 16 and 18 are each rotatable between the spaced arms forming the respective upper portion 82 of the screw 10 and the receiver 104 of the screw 12. The illustrated structures 16 and 18 are each substantially cylindrical and include an outer helically wound guide and advancement structure in the form of a flange form that operably joins with respective guide and advancement structures 88 and 106. A driving tool or tools (not shown) sized and shaped for engagement with a respective internal drive features 116 and/or 118 is used for both rotatable engagement and, if needed, disengagement of the closure 16 or 18 from the respective screw 10 or 12. The internal drive features 116 and 118 may take a variety of forms and may include, but is not limited to, a hex shape, TORX or other features or apertures, such as slotted, tri-wing, spanner, two or more apertures of various shapes, and the like.

As described in Applicant's '207 patent application disclosure, the closure 18 is sized and shaped to cooperate with and abut against the pressure insert 105 to lock the polyaxial mechanism thereof independent of any type or size of longitudinal connecting member, including an elastic or otherwise deformable longitudinal connecting member being held by the polyaxial bone screw 12. Depending on the closure top application, the closure top can lock both the polyaxial screw and the core or just the polyaxial screw, allowing the core to slide. The illustrated closure 18 includes an extended bottom surface 120 or rim that extends below the locking mechanism, fully engaging, and in the present embodiment compressing and deforming the core 4 within the polyaxial screw in a controlled and limited fashion, fixing the core 4 with respect to any axial motion with respect to the bone screw 12. In other embodiments, for example, if the central bone screw 10 of the assembly 1 is replaced by a polyaxial bone screw 12, an alternative to the closure 18 may be used that does not include the extending bottom surface, and would thus allow sliding of the core 4 with respect to such central bone screw 12, while the polyaxial mechanism of the screw 12 remains securely locked by the closure.

Figure 4A:
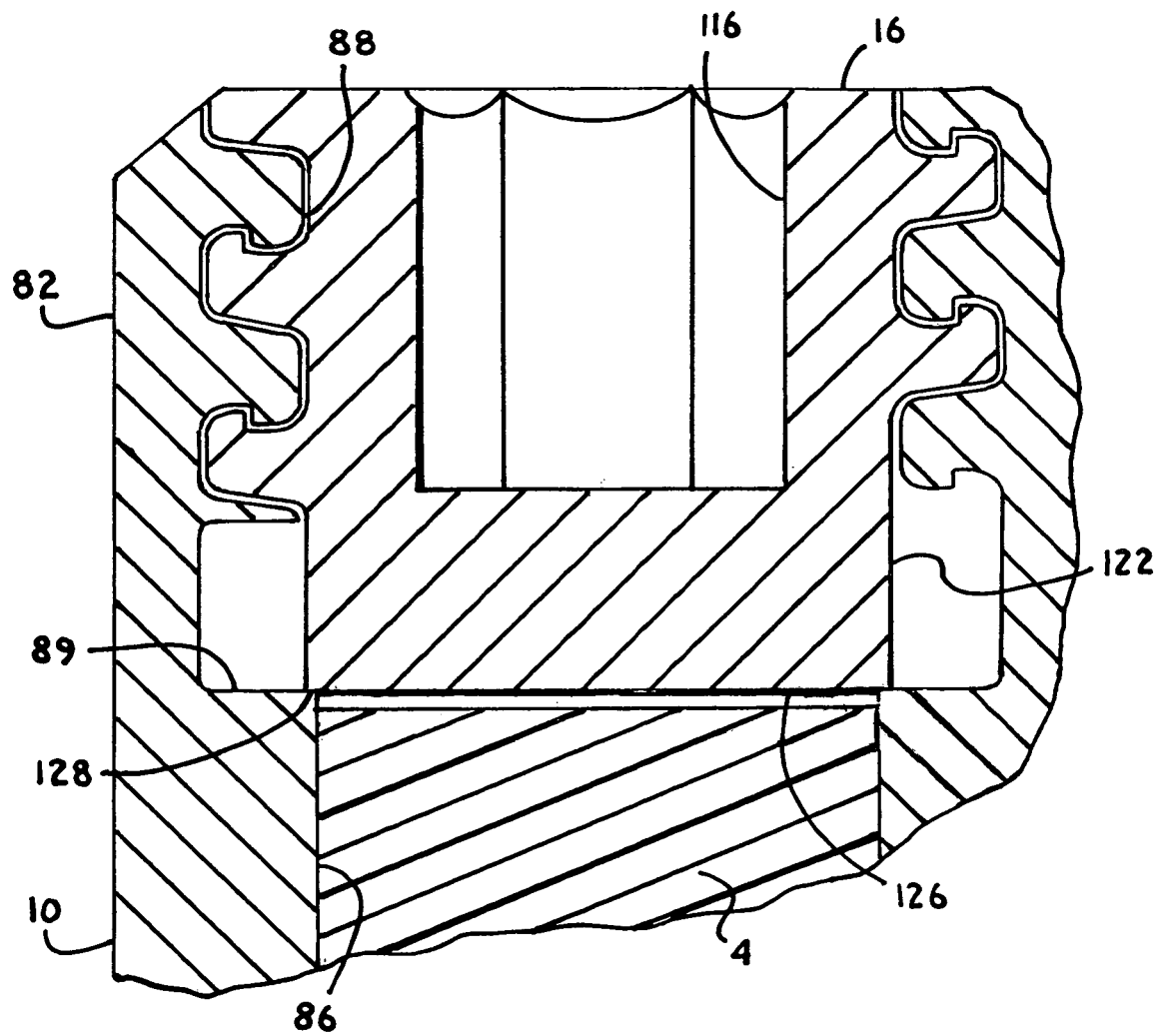
FIG. 4A is an enlarged and partial cross-sectional view taken along the line 4A-4A of FIG. 3 showing the closure top of the monoaxial bone screw.

With respect to the fixed screw 10, the cooperating closure 16 (shown in detail in FIG. 4A) is sized and shaped to cooperate with the run-out surface 89 to lock the closure 16 independent of any contact between the closure 16 on the flexible and sometimes deformable core 4. Again, the closure cooperating with the fixed screw 10 can be configured to lock the core 4 or not, as illustrated by the closure 16' of FIG. 4B, that does not allow the core 4 to slide. With particular reference to FIG. 4A, in the first illustrated embodiment, the closure 16 includes a first cylindrical surface 122 having a first diameter that is larger than a width defining the through channel 86 of the bone screw 10. The cylindrical surface 122 extends to a bottom planar surface 126. A perimeter or rim surface 128 of the planar surface 126 is located adjacent the surface 122. When the closure 16 is tightened by rotation into the screw 10, the surface 128 abuts against the surface 89, allowing the closure to be tightened in the screw 10 independent of any contact with the core 4. In the embodiment shown, the core 4 is in fact spaced from the closure bottom surface 126 and therefore is free to slide within the screw 10 while being fully captured thereby. The core 4 is thus protected against any compression and/or deformation or crushing by the closure 16 that might lead to damage and failure. Furthermore, even if the surface 126 is initially engaged with the core 4, if the core 4 exhibits creep or other deformation during operation, loosening or lessening of the contact engagement between the closure bottom surface 126 and the core 4 will not result in loosening and possible disengagement of the closure 16 from the screw 10, as well as displacement of the core out of the screw 10.

Figure 4B:
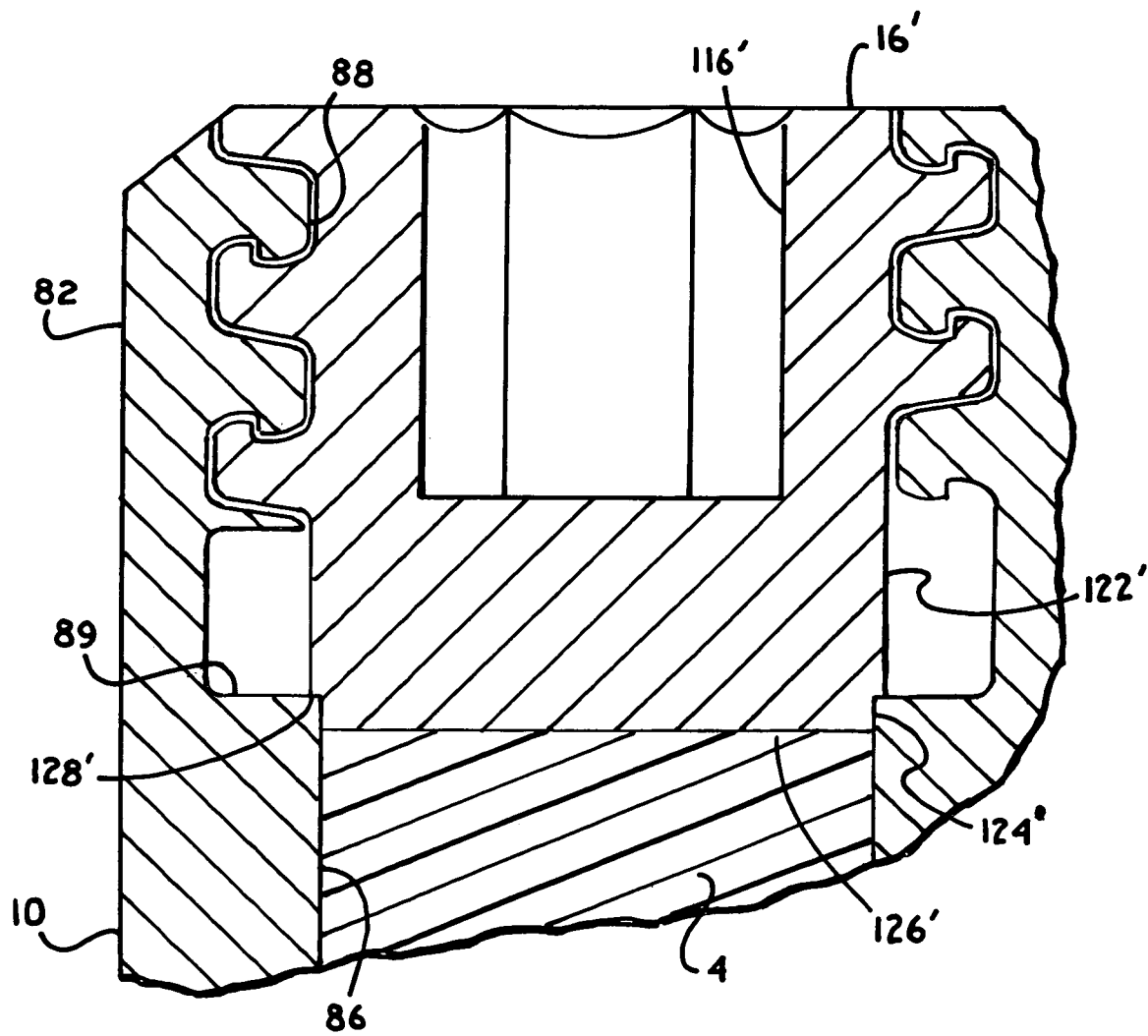
FIG. 4B is an enlarged and partial sectional view, similar to FIG. 4A, showing an alternative closure top for the monoaxial bone screw, and illustrated in use in FIG. 20.
Figure 12:
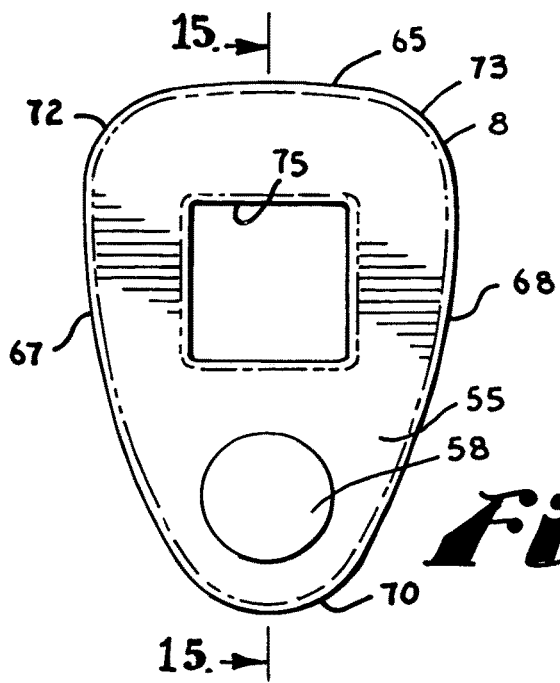
FIG. 12 is an enlarged front elevational view of one of the end caps of FIG. 1.
Figure 14:
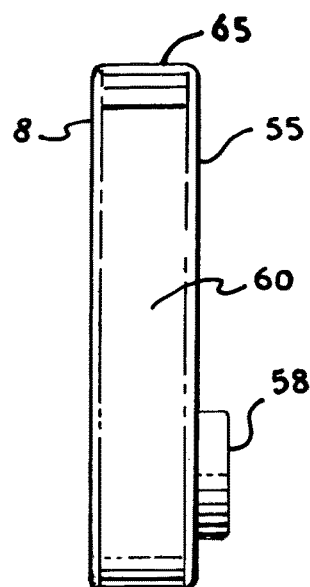
FIG. 14 is an enlarged side elevational view of the end cap of FIG. 12.
Figure 13:
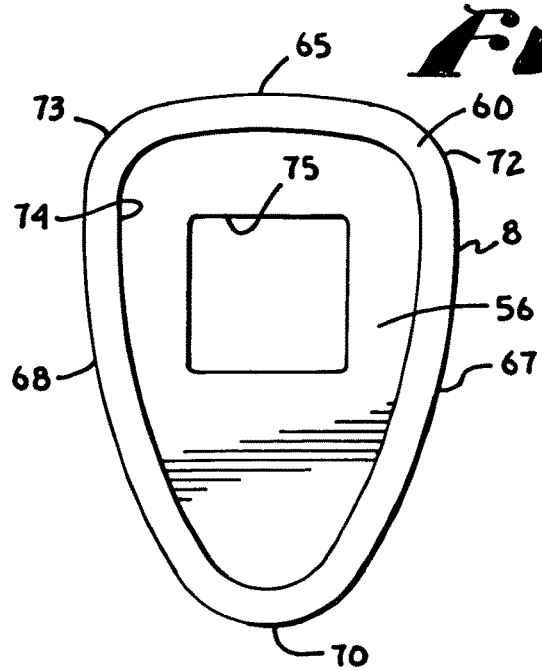
FIG. 13 is an enlarged rear elevational view of the end cap of FIG. 12.
Figure 15:
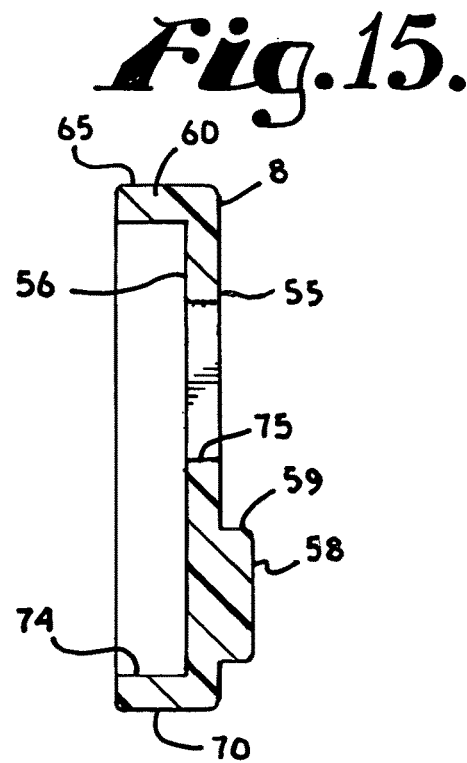
FIG. 15 is a cross-sectional view taken along the line 15-15 of FIG. 12.
Figure 16:
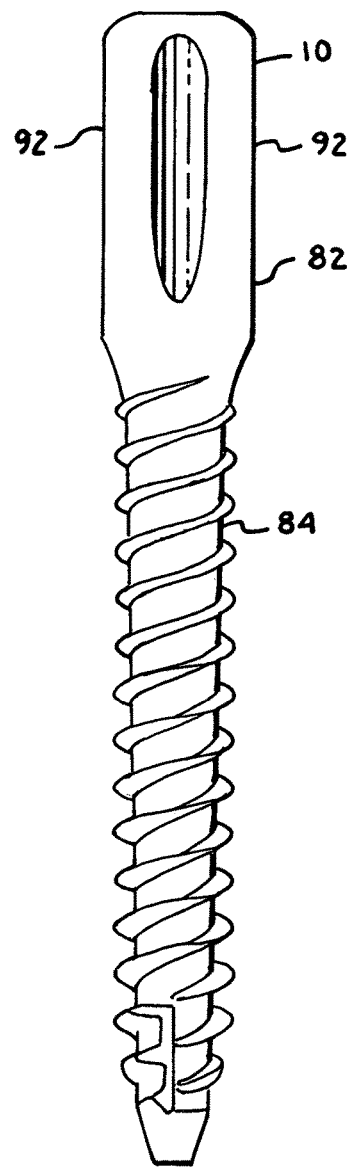
FIG. 16 is an enlarged side elevational view of the monoaxial bone screw of FIG. 1.
Figure 17:
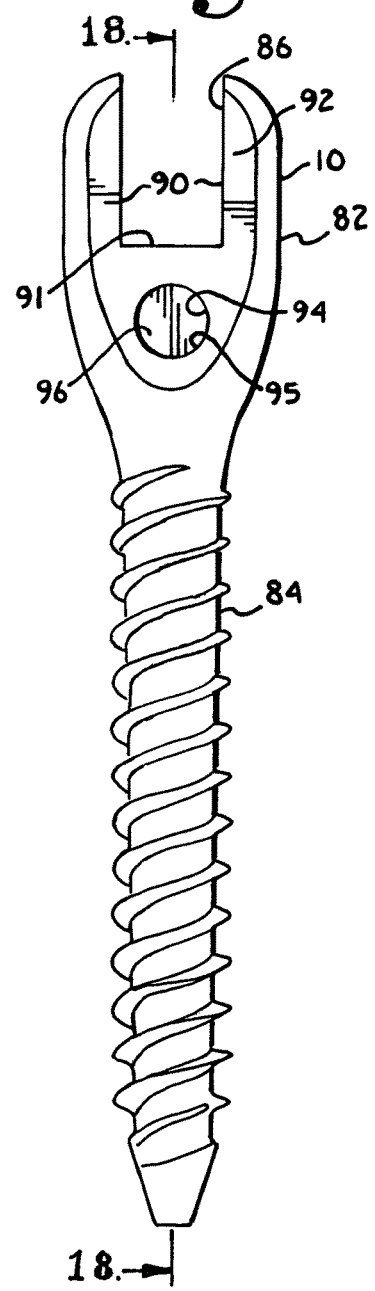
FIG. 17 is an enlarged front elevational view of the bone screw of FIG. 16.
Figure 18:
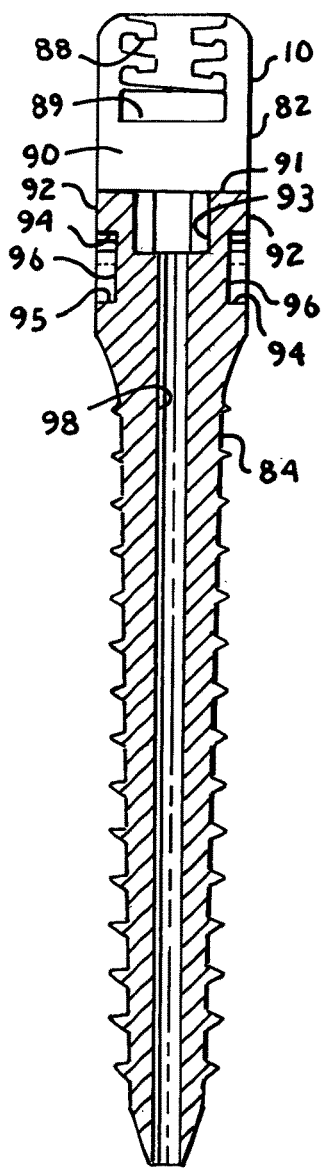
FIG. 18 is a cross-sectional view taken along the line 18-18 of FIG. 17.

If it is desired to have the closure of the fixed screw 10 engage and fix the core 4 (as shown, for example, in FIGS. 30 and 31), the closure 16' may be utilized with the screw 10 to capture and fix the core 4 there within. With reference to FIG. 4B, the closure 16' includes a first cylindrical surface 122' having a first diameter that is larger than a width defining the through channel 86 of the bone screw 10. The closure 16' further includes a second cylindrical surface 124' having a second diameter smaller than the first diameter of the surface 122'. The surface 122' represents the minor diameter of a major portion of the closure 16', while the second cylindrical surface 124' is located near a planar bottom surface 126' of the closure 16' that contacts and presses against the core 4' during operation, partially deforming the core 4'. A radially extending shelf or abutment seat 128' is formed between the first cylindrical surface 122' and the second cylindrical surface 124'. When the closure 16' is tightened by rotation into the screw 10, the seat 128' abuts against the surface 89, allowing the closure 16' to be tightened in the screw 10 independent of the core 4. In the embodiment shown, the core 4 is pressed upon and held in place by the surface 126' of the screw, with some deformation of the core 4 being acceptable and even desirable. However, because of the cooperation between the seat 128' and the screw surface 89, the core 4 is protected against over-deformation or crushing that might lead to damage and failure. Furthermore, if the core 4 exhibits creep or other deformation during operation, loosening or lessening of the contact engagement between the closure bottom surface 126' and the core 4 will not result in loosening and possible disengagement of the closure 16' from the screw 10. Again, it is foreseen that in certain embodiments the closure will be configured so that the seat 128' abuts against the surface 89 and tightens the screw, leaving the core 4 or other longitudinal connecting member, such as a cord or even a more rigid rod or bar to be operatively slidable within the channel 86 of the bone screw 10 and yet securely captured between the bone screw 10 and the closure 16 or 16'. For example, as shown in FIGS. 4 and 4A, the closure top 16 can close, but not lock the core 4 member in the screw head.

In use, the bone screws 10 and 12 are implanted into vertebrae for use with the flexible connecting member 13. Each vertebra may be pre-drilled to minimize stressing the bone. Furthermore, if a cannulated bone screw shank is utilized, each vertebra will have a guide wire or pin (not shown) inserted therein that is shaped for the bone screw cannula of the bone screw shanks 84 and 102 and provides a guide for the placement and angle of the shanks with respect to the cooperating vertebra. A further tap hole may be made and the shanks 84 and 102 are then driven into the vertebra by rotation of a driving tool (not shown) that engages the driving feature 93 or 103' of the respective screw 10 or 12. It is foreseen that the screws 10 and 12 and the flexible connector 13 can be inserted in a percutaneous or minimally or less invasive surgical manner.

With particular reference to FIGS. 1-4, the flexible connector 13 may be assembled by inserting the core 4 into an end cap 8, the core 4 being threaded through the through bore 75 at the surface 56, followed by insertion of the core 4 into the lumen 35 of the spacer 6. The spacer 6 is slid along the core 4 until the spacer end surface 37 abuts against the end cap 8 surface 56 and the curved sleeve 60 of the end cap 8 is disposed around the ovoid outer surface of the spacer 6 with the posterior portion 65 of the cap 8 being adjacent to the posterior surface 26 of the spacer 6, the side portion 68 of the cap 8 being adjacent the surface 27 of the spacer 6 and the side portion 67 of the cap 8 being adjacent to the side surface 28 of the spacer 6. At this time the end cap 8 and the spacer 6 are axially slidable with respect to one another along the core 4, but fixed with respect to rotation about the axis A of the core 4. Then, a second end cap 8 is threaded onto the core 4 with the surface 56 facing toward the surface 38 of the spacer 6. The second end cap 8 is slid along the core 4 until the surface 56 abuts against the spacer surface 38 and the curved sleeve 60 closely surrounds the spacer end portion 40. Similar to the first spacer 8, the opposing spacer 8 is disposed around the ovoid outer surface of the spacer 6 end portion 40 with the posterior portion 65 of the cap 8 aligning with the posterior surface 26 of the spacer 6, but with the side portion 67 of the cap 8 aligning with the surface 27 of the spacer 6 and the side portion 68 of the cap 8 aligning with the side surface 28 of the spacer 6. As with the first end cap 8, the second end cap 8 is now axially slidable with respect to the spacer 6, but rotation of the cap 8 with respect to the spacer 6 is prohibited. The spacer 7 and cooperating end caps 9 are similarly loaded onto the core 4. The flexible connector 13 is now assembled and ready for placement between the three bone screws 10 and 12 with the end cap pegs 58 directed outwardly from each spacer 6 or 7. In certain embodiments of the invention, the spacer 6 and cooperating end caps 8 may not be loaded onto the core 4 until after placement of the spacer 7 and end caps 9 between bone screws 10 and 12 or vice versa. In this way, different amounts of compression, if used, can be applied segmentally.

In the illustrated embodiment, the core 4 is received into respective open channels of the two polyaxial bone screws 12 and the fixed bone screw 10 with the spacer 6 and caps 8 between one pair of screws and the spacer 7 and caps 9 between an adjacent pair of screws with each of the pegs 58 of the caps 8 and 9 being inserted into an adjacent aperture 94 or 110 of a respective bone screw 10 or 12. Thereafter, the closures 16 and 18 are tightened, the closures 18 pressing into the core 4, and the closures 16 and 18 also independently locking with other components of the particular bone screw to ensure fixed engagement of the closure 16 and 18 with the respective bone screw regardless of creep or other further deformation of the core 4. Prior to engagement with the closures 16 and 18, the core 4 may be segmentally tensioned and the spacers 7 and 6 compressed, especially if the flexible core member 4 is a limp cord or cable. The resulting connecting member assembly 1 is thus dynamically loaded with the flexible core 4 preferably in tension and the pegs 58 in engagement with adjacent bone screws 10 and 12 at apertures 94 and 110, providing torsional and shear control. The assembly 1 is substantially dynamically loaded and oriented relative to the cooperating vertebra, providing relief (e.g., shock absorption), controlling torsional and shear forces and providing modified protected movement with respect to flexion, extension, distraction and compressive forces placed on the assembly 1.

If removal of the flexible connector 13 from the bone screws 10 and/or 12 is necessary, or if it is desired to release the assembly 13 at a particular location, disassembly is accomplished by using the driving tool (not shown) with a driving formation cooperating with the closure structure 16 and/or 18 to rotate and remove the respective closure structure from the respective bone screw 10 and/or 12. Disassembly is then accomplished in reverse order to the procedure described previously herein for assembly.

With particular reference to FIGS. 5 and 6, FIG. 5 illustrates an assembly 1 in a bended orientation as when responding to spinal extension, while FIG. 6 illustrates the same assembly 1 bending in response to spinal flexion. The figures illustrate the advantageous spread between the bone screw heads of the screws 10 and 12 during flexion of the spine 2 with a length L illustrating a distance between bone screws in FIG. 5 (extension) as compared to a longer length L' measured between the screws 10 and 12 in FIG. 6 (flexion).

Eventually, if the spine requires more rigid support, the connecting member assembly 13 according to the invention may be removed and replaced with another longitudinal connecting member, such as an inelastic (i.e., not stretchable or compressible) stiffer harder metal or plastic solid rod, having approximately the same diameter as a width of the core 4, utilizing the same bone screws 10 and 12. Alternatively, if less support is eventually required, a less stiff, more flexible assembly, for example, an assembly 13 made with elastic spacers of different durometer or geometry may replace the assembly 13, also utilizing the same bone screws 10 and 12. It is also foreseen that spacers may be used at some motion segments and not at others, as shown in FIGS. 19 and 20.

With reference to FIGS. 19 and 20, an alternative embodiment of a flexible longitudinal connecting member assembly, generally 1' is substantially similar to the assembly 1 with the exception that a core member 4' having a first end 22' and an opposed second end 24' is made from an alternative material to that of the core 4, the core 4' exhibiting slightly greater stiffness and less stretchability than the core member 4, for example, the illustrated core 4' is made from a polymer, such as PEEK. Furthermore, the assembly 1' does not include the spacer 6, the end caps 8 and one of the end caps 9 of the assembly 1. Also, the closure 16' is used in lieu of the closure 16 at the centrally located bone screw 10. Therefore in the assembly 1', all three closure tops 18 and 16' are engaged with and locked onto the core 4' as well as to the respective bone screw. The connecting member assembly 1' is otherwise identical to the assembly 1, using the same components, and thus all of the same features of those components have been given the same reference numbers as given above with respect to the assembly 1. The assembly 1' is also assembled in a manner substantially similar to the manner of assembly previously described herein with respect to the assembly 1. Even though the core 4' is not elastic, the core 4' is flexible and may be tensioned between the bone screws 10 and 12 and the spacer 7 therebetween placed in compression.

Figure 21:
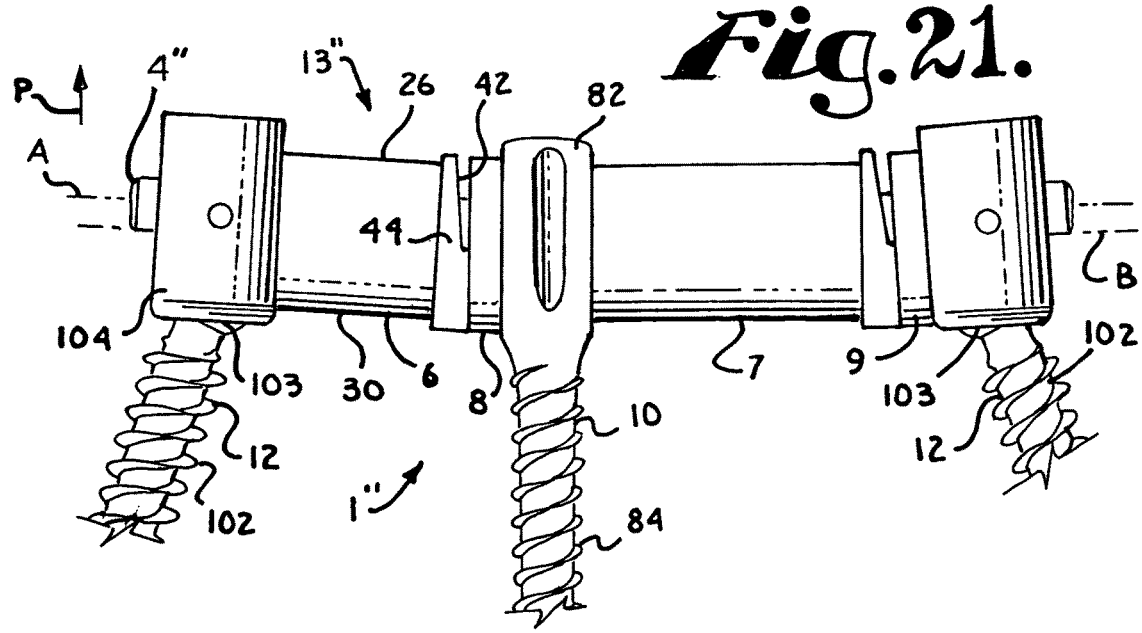
FIG. 21 is an enlarged and partial side elevational view of another alternative embodiment of a flexible stabilization assembly and cooperating bone screws according to the invention.
Figure 22:
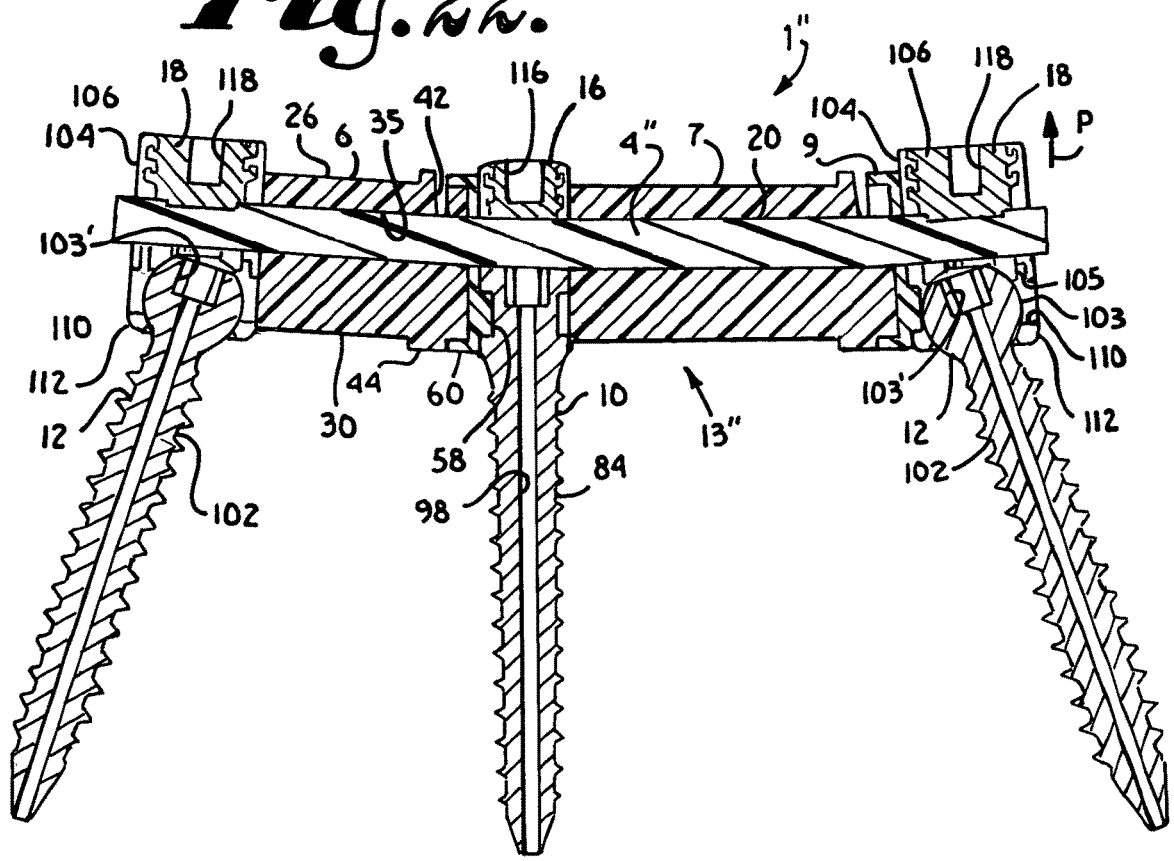
FIG. 22 is another enlarged side elevational view of the assembly and bone screws of FIG. 21 with portions broken away to show the detail thereof.
Figure 23:
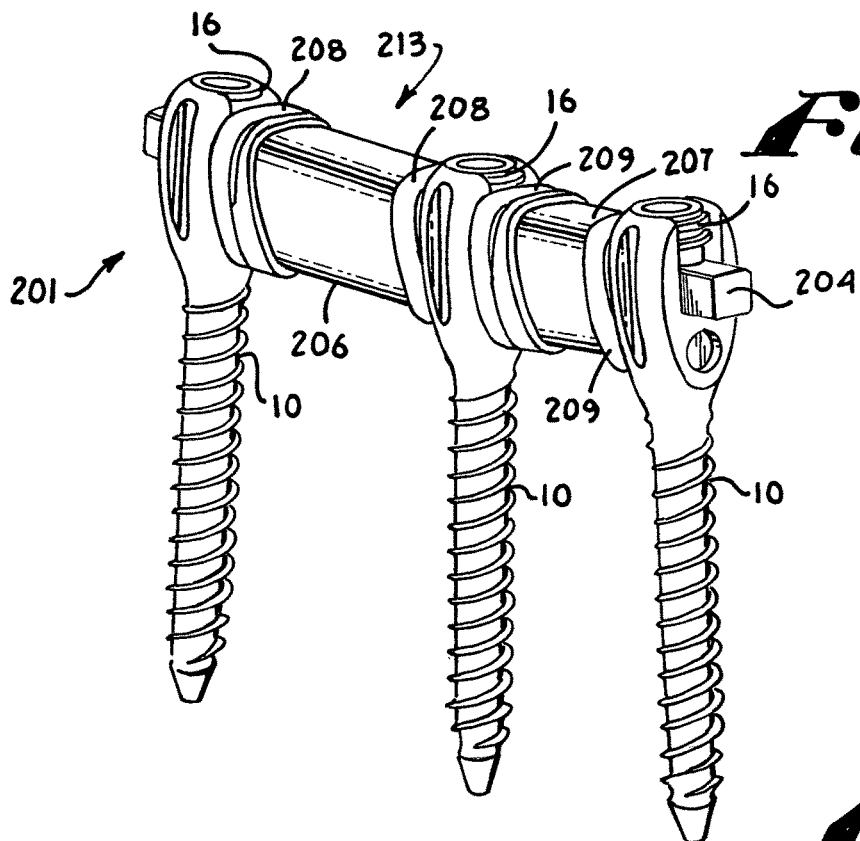
FIG. 23 is an enlarged perspective view of another alternative embodiment of a flexible stabilization assembly and cooperating bone screws according to the invention.
Figure 24:
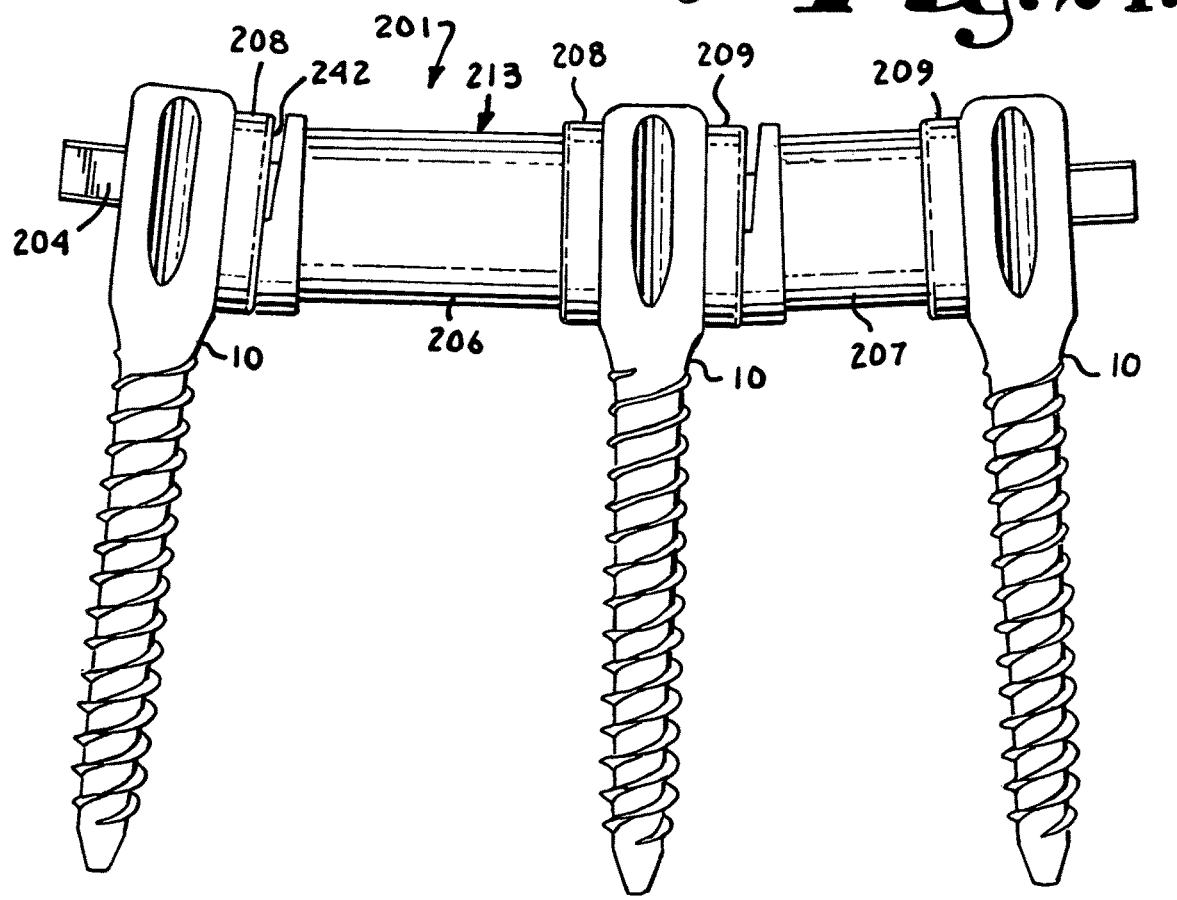
FIG. 24 is an enlarged side elevational view of the assembly and bone screws of FIG. 23.
Figure 25:
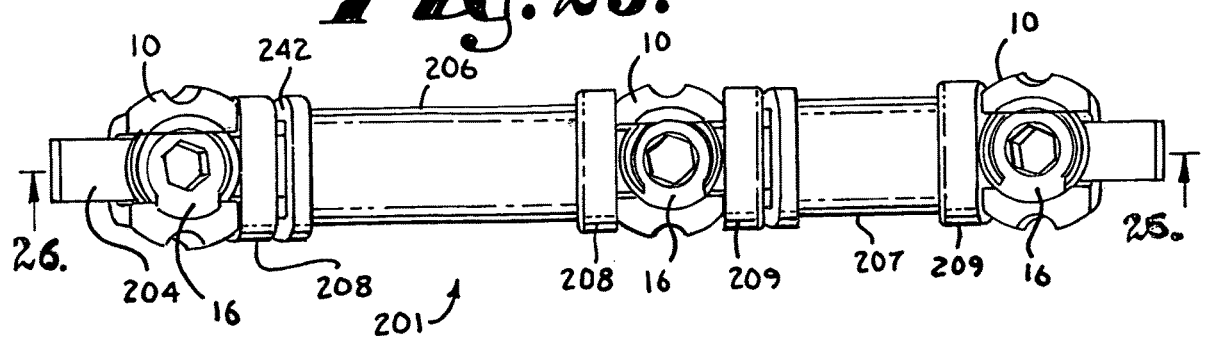
FIG. 25 is an enlarged top plan view of the assembly and bone screws of FIG. 23.
Figure 26:
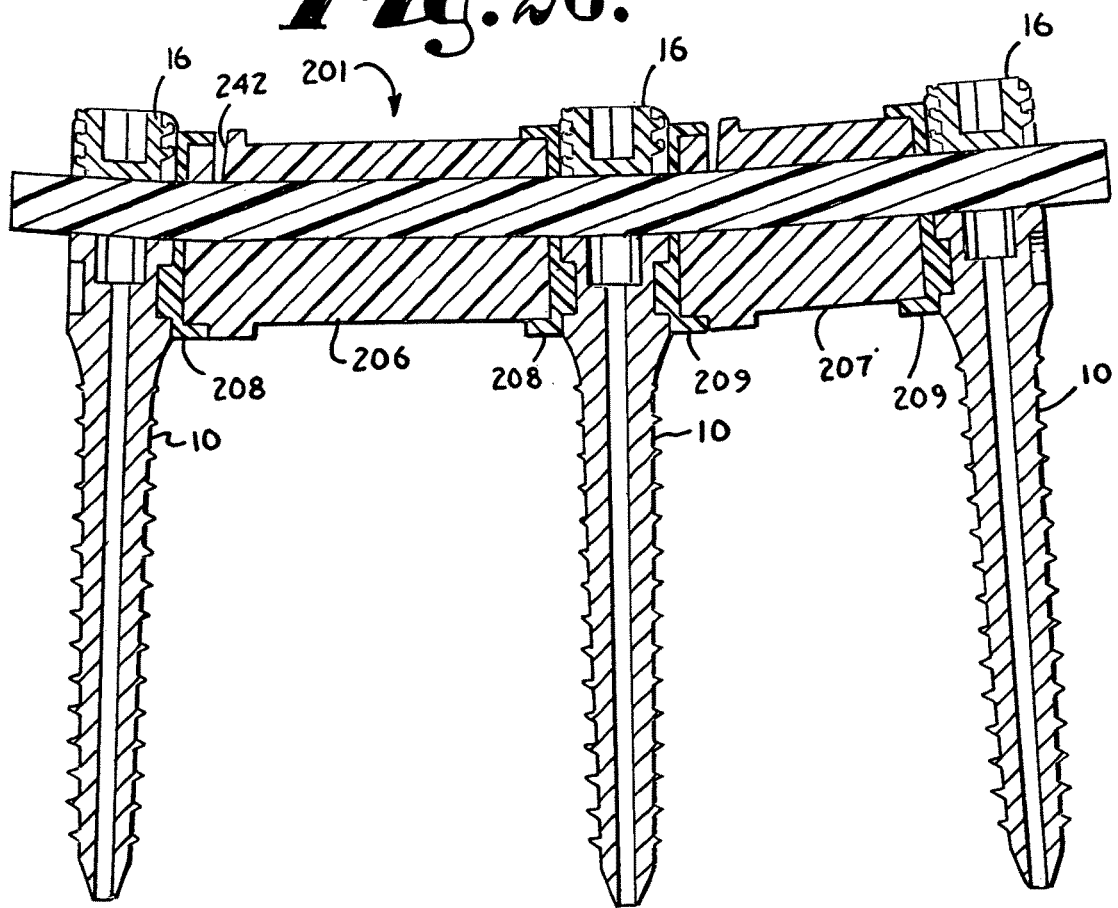
FIG. 26 is an enlarged cross-sectional view taken along the line 26-26 of FIG. 25.

With reference to FIGS. 21 and 22, another alternative embodiment of a flexible longitudinal connecting member assembly, generally 1" is substantially similar to the assembly 1 with the exception that one optional end cap 8 and one optional end cap 9 have been removed. The spacer 6 therefore abuts directly against one bone screw 12 and the spacer 7 abuts directly against the bone screw 10. The core member 4" may be the same or different from the core member 4. For example, in the illustrated assembly 1", the core 4" is a limp cord that is pre-tensioned. Similar to the assembly 1, the assembly 1" central bone screw 10 cooperates with the closure 16 that captures the core 411, but also allows the core 4" to slide with respect to the screw 10. The connecting member assembly 111 is otherwise identical to the assembly 1, using the same components, and thus all of the same features of those components have been given the same reference numbers as given above with respect to the assembly 1. The assembly 1" is also assembled in a manner substantially similar to the manner of assembly previously described herein with respect to the assembly 1.

With reference to FIGS. 23-26, another alternative embodiment of a flexible longitudinal connecting member assembly, generally 201 is substantially similar to the assembly 1 with the exception that three monoaxial bone screws 10 and cooperating closures 16 and 16' are shown with a connecting member 213 having spacers 206 and 207 that are identical to the spacers 6 and 7 of the assembly 1, but are of a slightly different length measured along a core 204. Similar to the assembly 1, the assembly 201 core 204 is substantially similar or identical to the core 4 of the assembly 1. Furthermore, the core 4 is allowed to slide with respect to the centrally located screw 10 that cooperates with the closure 16, while the closures 16' engage and lock the core 4 in place at each of the end or outer screws 10. The assembly further includes end caps 208 and 209 that are substantially similar or identical to the caps 8 and 9 of the assembly 1. The assembly 201 is also assembled in a manner substantially similar to the manner of assembly previously described herein with respect to the assembly 1.

Figure 30:
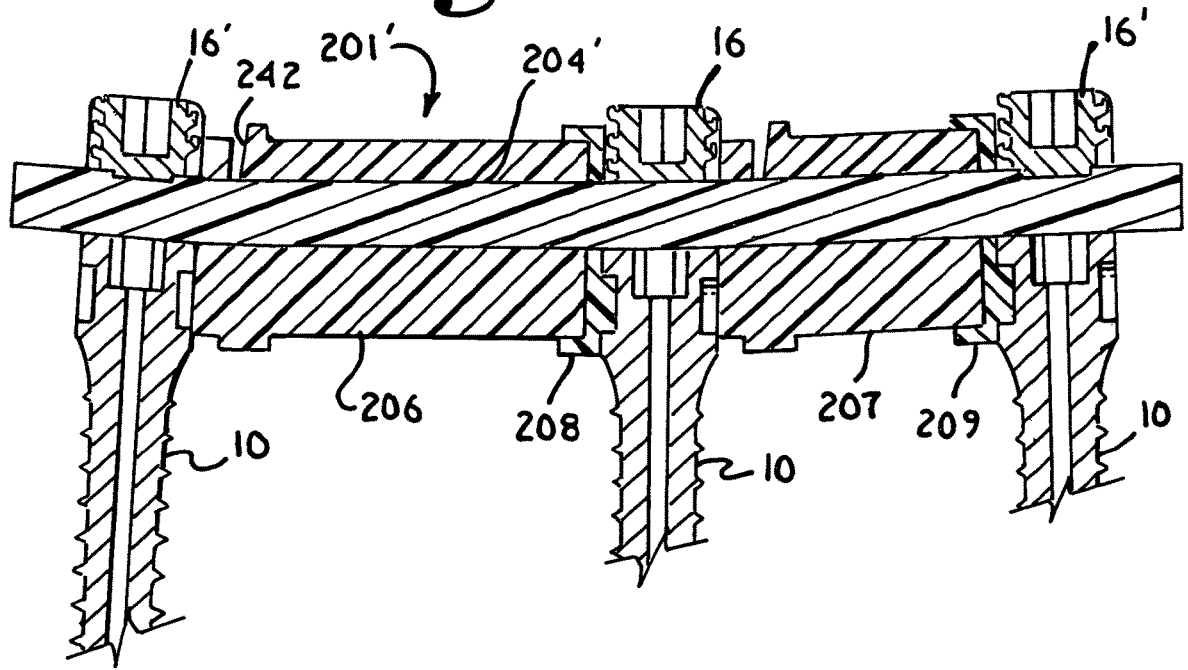
FIG. 30 is an enlarged and partial side elevational view of another alternative embodiment of a flexible stabilization assembly and cooperating bone screws according to the invention, with portions broken away to show the detail thereof.

With reference to FIG. 30, another alternative embodiment of a flexible longitudinal connecting member assembly, generally 201' is substantially similar to the assembly 201 with the exception that one optional end cap 208 and one optional end cap 209 have been removed. The spacer 206 therefore abuts directly against one bone screw 10 and the spacer 207 abuts directly against an adjacent bone screw 10. The core 204' may be made of the same or different materials from the core 204, the core 204' being shown slidable with respect to the middle screw 10 and cooperating closure 16. The connecting member assembly 201' is otherwise identical to the assembly 201, using the same components, and thus all of the same features of those components have been given the same reference numbers as given above with respect to the assembly 201. The assembly 201' is also assembled in a manner substantially similar to the manner of assembly previously described herein with respect to the assembly 201 and the assembly 1.

Figure 31:
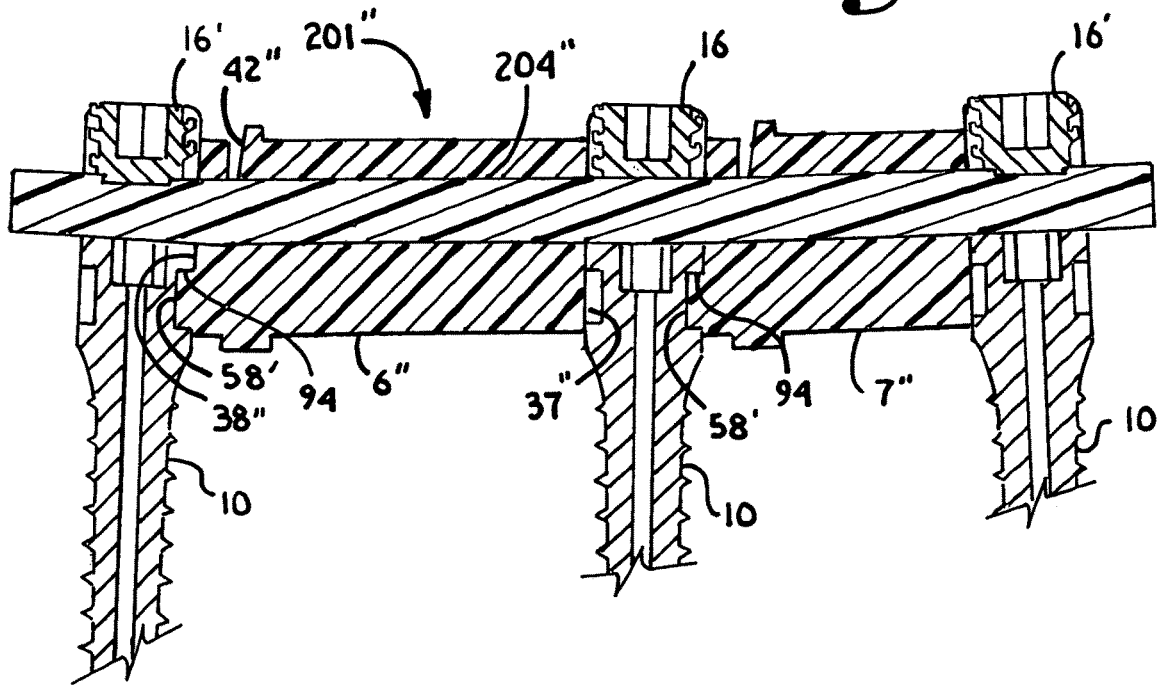
FIG. 31 is an enlarged and partial side elevational view of another alternative embodiment of a flexible stabilization assembly, including the spacer of FIG. 29 and cooperating bone screws according to the invention, with portions broken away to show the detail thereof.

With reference to FIG. 31, another alternative embodiment of a flexible longitudinal connecting member assembly, generally 201" is substantially similar to the assembly 201 with the exception that all of the end caps 208 and 209 have been removed and the spacers 206 and 207 have been replaced with spacers 6" and 7". The spacer 6" is shown in FIG. 29 and has been previously described herein. The spacer 7" is shorter in axial length than the spacer 6", but is otherwise identical to the spacer 6". Each of the spacers 6" and 7" have a peg 58' received within the aperture 94 of an adjacent, abutting bone screw 10. The core 204" may be made of the same or different materials from the core 204, the core 204" being shown slidable with respect to the middle screw 10 and cooperating closure 16. However, in other embodiments, the closure 16' may be used to lock the core 204" within the middle screw 10.

It is foreseen that the spacer of the invention could be provided in many different sizes and shapes and lengths and that the spacer could be used with no end caps and no peg-like projections; or, with peg-like integral projections on both ends. The shape of the spacer could keep such spacer positioned or oriented correctly, with or without a square shaped lumen, when used without any pegs and without any end caps.

It is to be understood that while certain forms of the present invention have been illustrated and described herein, it is not to be limited to the specific forms or arrangement of parts described and shown.

What is claimed and desired to be secured by Letters Patent is as follows:

1. A medical implant assembly including at least first and second bone anchors each having a channel, the channels receiving and cooperating with a longitudinal connecting member captured in the channels by closures, the longitudinal connecting member comprising:
   i) a spacer having an off-axis through-bore disposed between the first and second bone anchors, the spacer having:
      first and second end surfaces, at least one of the first and second end surfaces facing toward one of the first and second bone anchors,
      an anterior region and a posterior region, the off-axis through-bore located more toward the posterior region and running between and entirely through the first and second end surfaces and the anterior and posterior regions, the spacer being more compressible along the posterior region than the anterior region;
   ii) a support structure located about at least a portion of an outer surface of the spacer to provide anterior support near an end surface of the spacer;
   iii) a tensionable inner core slidingly receivable in the off-axis through bore and being in slidable relation with respect to at least one of the bone anchors when the closures are tightened down and capturing the longitudinal connecting member in the channels; and
   iv) an end cap disposed between the spacer and the first bone anchor, the end cap having a through-bore and mating with the spacer, so as to resist torsion therebetween on the first end surface of the spacer thereof, the end cap mating with the first anchor on an end cap first end surface, so as to resist torsion therebetween prior to insertion of a closure into the first bone anchor channel, and wherein the end cap includes at least one protrusion and the first bone anchor has a protrusion receiving structure thereon, and wherein the support structure is sized and shaped to mate with the end cap.

2. The medical implant assembly of claim 1, wherein the medical implant assembly is implantable such that the tensionable inner core is disposed at a posterior location with respect to a central axis of the spacer, the posterior location of the tensionable inner core compressing the spacer more posteriorly than anteriorly when tensioned.

3. The medical implant assembly of claim 1, wherein the spacer includes a maximum height extending between a posterior side and an anterior side, the maximum height being greater than a maximum width of the spacer extending in a direction transverse to the maximum height and along a length of the spacer.

4. The medical implant assembly of claim 1, wherein the off-axis through-bore has a constant diameter.

5. The medical implant assembly of claim 1, wherein the tensionable inner core is in direct engagement with at least one of the bone anchor channels.

6. The medical implant assembly of claim 1, wherein at least one of the bone anchors is cannulated along an entire length thereof.

7. The medical implant assembly of claim 1, wherein the support structure encircles at least a portion of the perimeter of the spacer.

8. The medical implant assembly of claim 1, wherein the support structure comprises a rim disposed near at least one of the first and second end surfaces.

9. The medical Implant assembly of claim 1, wherein the support structure comprises at least one groove in a surface thereof.

* * * * *